(12) United States Patent
Katz et al.

(10) Patent No.: US 8,093,001 B2
(45) Date of Patent: *Jan. 10, 2012

(54) DETECTION AND DIAGNOSIS OF SMOKING RELATED CANCERS

(75) Inventors: Ruth Katz, Houston, TX (US); Feng Jiang, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/761,134

(22) Filed: Apr. 15, 2010

(65) Prior Publication Data

US 2010/0240060 A1 Sep. 23, 2010

Related U.S. Application Data

(63) Continuation of application No. 10/952,251, filed on Sep. 28, 2004, now Pat. No. 7,741,034, which is a continuation of application No. 09/923,304, filed on Aug. 6, 2001, now Pat. No. 6,797,471.

(60) Provisional application No. 60/222,811, filed on Aug. 4, 2000.

(51) Int. Cl.
*C07H 21/04* (2006.01)
*C12Q 1/68* (2006.01)

(52) U.S. Cl. ...... 435/6.1; 435/6.11; 435/6.14; 435/91.1; 435/91.2; 536/23.1; 536/24.3

(58) Field of Classification Search .................. None
See application file for complete search history.

(56) References Cited

U.S. PATENT DOCUMENTS

| | | | |
|---|---|---|---|
| 5,670,314 A | 9/1997 | Christman et al. | 435/6 |
| 6,174,681 B1 | 1/2001 | Halling et al. | 435/6 |
| 6,344,315 B1 | 2/2002 | Gray et al. | 435/6 |
| 6,376,188 B1 | 4/2002 | Halling et al. | 435/6 |
| 6,475,720 B1 | 11/2002 | Gray et al. | 435/6 |
| 6,576,420 B1 | 6/2003 | Carson et al. | 435/6 |
| 6,689,561 B1 | 2/2004 | Carson et al. | 435/6 |
| 6,780,592 B2 | 8/2004 | Sidransky | 435/6 |
| 6,797,471 B2 * | 9/2004 | Katz et al. | 435/6 |
| 6,846,650 B2 | 1/2005 | Recipon et al. | 435/69.1 |
| 2002/0160409 A1 | 10/2002 | Halling et al. | 435/6 |
| 2003/0087248 A1 | 5/2003 | Morrison et al. | 435/6 |
| 2003/0119080 A1 | 6/2003 | Mangano | 435/7.23 |
| 2003/0138928 A1 | 7/2003 | Carson et al. | 435/184 |
| 2004/0126398 A1 | 7/2004 | Jager et al. | 424/277.1 |
| 2006/0171567 A1 | 8/2006 | Osher et al. | 382/106 |

FOREIGN PATENT DOCUMENTS

| WO | WO 01/38389 | 5/2001 |
|---|---|---|
| WO | WO 02/12563 | 2/2002 |

OTHER PUBLICATIONS

Thiberville et al. (Int. J. Cancer, vol. 64, pp. 371-377, 1995).*
Shriver et al. (Mutation Research Genomics, vol. 406, No. 1, pp. 9-23, Nov. 1998).*
Wu et al. (Cancer Research, vol. 58, pp. 1605-1608, 1998).*
Honda et al. (Hum. Genet. vol. 105, pp. 428-436, 1999).*
Alberola et al., "Prognostic significance of flow cytometry and EGFR in resectable non-small cell lung cancer (NSCLC): results of a prospective study," *Proc. Annu. Mt. Am. Soc. Clin. Oncol.*, 14: 359, Abstract A1094, 1995.
Alimov et al., "Combined LOH/CGH analysis proves the existence of interstitial 3p deletions in renal cell carcinoma," *Oncogene*, 19:1392-1399, 2000.
Auerbach et al., "Changes in bronchial epithelium in relation to cigarette smoking and in relation to lung cancer," *N. Engl J. Med.*, 265: 253-267, 1961.
Ayabe et al., "DNA stemline heterogencity of non-small cell lung carcinomas and differences in DNA polidy between carcinomas and metastactic nodes," *Lung Cancer*, 11(3-4): 201-208, 1994.
Barinaga, "An intriguing new lead on Huntington's Disease," *Science*, 271: 1233-1234, 1996.
Barkan et al., "Comparison of molecular abnormalities in bronchial brushings and tumor touch preparations," *Cancer*, 105:35-43, 2005.
Bartlett et al., "Evaluating HER2 amplification and overexpression in breast cancer," *J. Pathology*, 195:422-428, 2001.
Bepler et al., "Association of chromosome 11 locus D11S12 with histology, stage, and metastases lung cancer," *Cancer Detection and Prevention*, 22(1):14-29, 1998.
Bissola et al., "Association of chromosome 10 losses and negative prognosis in oligoastrocytomas," *Annals of Neurology*, 52(6):842-845, 2002.
Bockmuhl et al., "Deletion of chromosome 10q—a marker for metastasis of head-neck carcinomas?" *Laryngorhinootologie*, 79(2):81-85, 2000, article in German, English abstract included.
Brock et al., Detection of numerical chromosome anomalies in interphase cells of ovarian carcinomas using fluorescence in situ hybridization, *Genes, Chromosomes and Cancer*, 16:120-129, 1996.
Brugal et al., "Image analysis of microscopic preparations," *Method Achiev. Exp. Pathol.*, 11: 1-33, 1984.
Cairns et al., "Genomic organization and mutation analysis of *Hel-N1* in lung cancers with chromosome 9p21 deletions," *Cancer Res*, 57:5356-5359, 1997.
Carney et al., "Influence of histologic subtype of small cell carcinoma of the lung on clinical presentation, response to therapy and survival," *JNCI*, 65:1225-1230, 1980.
Carriaga et al., "The histologic grading of cancer," *Cancer*, 75:406-421, 1995.
Chanin et al., "Recent developments in biomarkers for the early detection of lung cancer: perspectives based on publications 2003 to present," *Current Opinion in Pulmonary Medicine*, 10:242-247, 2004.

(Continued)

*Primary Examiner* — Jeanine A Goldberg
(74) *Attorney, Agent, or Firm* — Fulbright & Jaworski L.L.P.

(57) ABSTRACT

Gene probes for specific regions of chromosome 3 (3p21.3) and chromosome 10 (10q22) have been found to be tools for the diagnosis and prognosis of smoking related cancers such as non-small cell lung cancer (NSCLC). For example, these probes can be used with fluorescence in situ hybridization (FISH), and used to stratify smokers into high and low risk groups, as well as determine a patients susceptibility to the development of smoking related cancers.

26 Claims, 9 Drawing Sheets

OTHER PUBLICATIONS

Cheon et al., "Flow cytometric analysis of DNA ploidy in primary non-small cell lung carcinoma of the lung in Korea," *Yonsei Med. J.*, 34(4): 365-370, 1993.

Chung et al., "Loss of heterozygosity at the short arm of chromosome 3 in microdissected cervical intraepithelial neoplasia," *Cancer Letters*, 154:189-194, 2000.

Clark et al., "Genome-wide screening for complete genetic loss in prostate cancer by comparative hybridization onto cDNA microarrays," *Oncogene*, 22:1247-1252, 2003.

Czerniak et al., "Genetic model of human urinary bladder carcinogenesis," *Genes, Chromosomes, and Cancer*, 27:392-402, 2000.

Czerniak et al., "Superimposed histologic and genetic mapping of chromosome 9 in progression of human urinary bladder neoplasia: implications for a genetic model of multistep urothelial carcinogenesis and early detection of urinary bladder cancer," *Oncogene*, 18:1185-1196, 1999.

Dalquen et al., "DNA aneuploidy, s-phase fraction, nuclear p53 positivity, and survival in non-small-cell lung carcinoma," *Virchows Archiv.*, 431(3): 173-179, 1997.

Daly et al., "A homozygous deletion on chromosomes 3 in small cell lung cancer cell line correlates with a region of tumor suppressor activity," *Oncogene*, 8(7):1721-1729, 1993.

Daniely et al., "Combined analysis of morphology and fluorescence in situ hybridization significantly increases accuracy of bladder cancer detection in vodied urine samples," *Urology*, 66:1354-1359, 2005.

Döbler et al., "Deletion monitoring in skin tumors by interphase-FISH using band-specific DNA probes," *International Journal of Oncology*, 14:571-576, 1999.

Dong et al., "KAI1 a metastasis suppressor gene for prostate cancer on human chromosome 11p11.2," *Science*, 268:884-886, 1995.

El-Zein et al., "Chromosomal instability in peripheral blood lymphocytes and risk of prostate cancer," *Cancer Epidemiol Biomarkers Prev*, 14:748-752, 2005.

Fan and Rizkalla, "Comprehensive cytogenetic analysis including multicolor spectral karyotyping and interphase fluorescence in situ hybridization in lymphoma diagnosis: a summary of 154 cases," *Cancer Genetics and Cytogenetics*, 143:73-79, 2003.

Fawole et al., "Loss of heterozygosity on chromosome 10q is associated with earlier onset sporadic colorectal adenocarcinoma," *Int. J. Cancer*, 99:829-833, 2002.

Feder et al., "Clinical relevance of chromosome abnormalities in non-small cell lung cancer," *Cancer Genet. Cytogenet.*, 102: 25-31, 1998.

Feinstein et al., "Observer variability in the histopathologic diagnosis of lung cancer," *Am Rev Repir Dis*, 101:671-684, 1970.

Feinstein et al., "The diverse effects of histopathology on manifestations and outcome of lung cancer," *Chest*, 66(3):225-229, 1974.

Field et al., "Genetic alterations in bronchial lavage as a potential marker for individuals with a high risk of developing lung cancer," *Can Res.*, 59:2690-2695, 1999.

Fontanini et al., "The expression of proliferating cell nuclear antigen in paraffin sections of peripheral, Node-negative non-small cell lung cancer," *Cancer*, 70(6): 1520-1527, 1992.

Frayling et al., "Allele loss in colorectal cancer at the cowden disease/juvenile *Polyposis locus* on 10q," *Cancer Genet Cytogenet*, 97:64-69, 1997.

Fujita et al., "Expression of thyroid transcription factor-1 in 16 human lung cancer cell lines," *Lung Cancer*, 39:31-36, 2003.

Furlan et al, "Allelotypes and fluorescence in situ hybridization profiles of poorly different sites," *Clinical Cancer Research*, 11:1765-1775, 2005.

Gasparotto et al., "Loss of heterozygosity at 10q in tumors of the upper respiratory tract is associated with poor prognosis," *Int. J. Cancer*, 84:432-6, 1999.

Hagmar et al., "Cancer risk in humans predicted by increased levels of chromosomal aberrations in lymphocytes: nordic study group on the health risk of chromosome damage," *Cancer Res*, 54:2919-2922, 1994.

Harbeck et al., "HER-2/neu gene amplification by fluorescence in situ hybridization allows risk-group assessment in node-negative breast cancer," *Intl. J. Oncology*, 14:663-671, 1999.

Hirano et al., "Genesis of squamous cell lung carcinoma. Sequential changes of proliferation, DNA ploidy, and p53 expression," *American J. Path.*, 144(2): 296-302, 1994.

Hirsch et al., "Intracranial metastases in small cell carcinoma of the lung," *Cancer*, 51:529-533, 1983.

Hirsch et al., "The prognostic significance of histopathologic subtyping of small cell carcinoma of the lung according to the classification of the world health orgainization," *Cancer*, 52:2144-2150, 1983.

Hofmann et al., "Matrix metalloproteinase-12 expression correlates with local recurrence and metastatic disease in non-small cell lung cancer patients," *Clinical Cancer Research*, 11:1086-1092, 2005.

Hosoya et al., "Alteration of the PTEN/MMAC1 gene *locus* in primary lung cancer with distant metastasis," *Lung Cancer*, 25:87-93, 1999.

Hung et al., "Allele-specific chromosome 3p deletions occur at an early stage in the pathogenesis of lung carcinoma," *JAMA*, 273(7):558-563, 1995.

Ichinose et al., "Postoperative adjuvant chemotherapy in non-small cell lung cancer: prognostic value of DNA ploidy and post-recurrent survival," *J. Surgical Oncology*, 46(1): 15-20, 1991.

Ihde, "Non-small cell lung cancer. Biology, diagnosis and staging," *Curr. Prob. Cancer*, 15:63-104 1991.

Ji et al., "Expression of several genes in the human chromosome 3p21.3 homozygous deletion region by an adenovirus vector in tumor suppressor activities in vitro and in vivo," *Cancer Research*, 62:2715-2720, 2002.

Jiang and Katz, "Use of interphase fluorescence in situ hybridization as a powerful diagnostic tool in cytology," *Diagn. Mol. Pathol.*, 11:47-57, 2002.

Jiang et al., "Genomic profiles in stage I primary non small cell lung cancer using comparative genomic hybridization analysis of cDNA microarrays," *Neoplasia*, 6:623-635, 2004.

Jiang et al., "Surfactant protein a gene deletion and prognostics for patients with state I non small cell lung cancer," *Clinical Cancer Research*, 11:5417-5424, 2005.

Junker et al., "Genetic characterization of lung metastases in renal cell carcinoma," *Oncology Reports*, 10:1035-1038, 2003.

Kim et al., "Alterations of PTEN/MMAC1, a candidate tumor suppressor gene, and its homologue, PTH2, in small cell lung cancer cell lines," *Oncogene*, 16:89-93, 1998.

Kim et al., "DNA ploidy and proliferative activity in bcl-2 expressed non-small cell lung cancer," *Korean J. Intern. Med*, 11(2):101-107, 1996.

Kinoh et al., "Assignment of the genes for membrane-type-4 matrix metalloproteinase (Mmp17, MMP17) to mouse chromosome 5, human chromosome band 12q24.3 and membrane-type-5 matrix metalloproteinase (Mmp24, MMP24) to mouse chromosome 2 and human chromosome band 20q11.2—>q12, respectively, by radiation hybrid and in situ hybridization," *Cytogenet Cell Genet.*, 87:97-98, 1999.

Kleist et al., "Multiple chromosomal underrespresentations detected by interphase cytogenetics: possible prognostic markers in head and neck tumors?," *Pathology Oncology Research*, 7:28-32, 2001.

Korbling et al., "Hepatocytes and epithelial cells of donor origin in recipients of peripheral-blood stem cells," *N. Engl. J. Med.*, 346:738-746, 2002.

Kotton et al., "Bone marrow-derived cells as progenitors of lung alveolar epithelium," *Development*, 128:5181-5188, 2001.

Lee et al., "Human retinoblastoma susceptibility gene: cloning, identification, and sequence," *Science*, 235:1394-1399, 1987.

Licciardello et al., "Multiple primary cancer in patients with cancer of the head and neck: second cancer in the head and neck, esophagus and lung," *Int. J. Radiat. Oncol. Bio. Phys.*, 17: 467-476, 1989.

Liewald et al., "Flow cytometric analysis of non-small-cell bronchial carcinoma and its prognostic significance," *Chirurg*, 63(3): 205-210, 1992, Article in German, English abstract included.

Lifton, "Molecular genetics of human blood pressure variation," *Science*, 272: 676-680, 1996.

Lingle et al., "Centrosome amplification drives chromosomal instability in breast tumor development," *PNAS*, 99:1978-1983, 2002.

Linnoila et al., "Expression of surfactant-associated protein in non-small-cell lung cancer: a discriminant between biologic subsets," *J. Natl. Cancer Instit. Monographs*, 61-66, 1992.

Llano et al., "Identification and characterization of human MT5-MMP, a new membrane-bound activator of progelatinase a overexpressed in brain tumors," *Cancer Res.*, 59:2570-2576, 1999.

Lukas et al., "Retinoblastoma-protein-dependent cell-cycle inhibition by the tumour suppressor p. 16," *Nature* 375(6531):503-6, 1995.

Macchiarini et al, "Risk of cancer recurrence in completely resected T1N0M0 non-small cell lung cancer (NSCLC)," *Proc Annu Mt. Am. Soc. Clin. Oncol.* 11:297, abstract # 995, 1992.

Miki et al., "A strong candidate for the breast and ovarian cancer susceptibility gene BRCA1," *Science*, 266: 66-71, 1994.

Mitsudomi et al., "Loss of heterozygosity at 3p in non-small cell lung cancer and its prognostic implication," *Clin. Cancer Res.*, 2(7): 1185-1189, 1996.

Miura et al., "Chromosome alterations in 21 non-small cell lung carcinomas," *Genes Chromosomes Cancer*, 2(4):328-338, 1990.

Miyamoto et al., "Prognostic value of nuclear DNA content and expression of the RAS oncogene product in lung cancer," *Cancer Research*, 51: 6346-6350, 1991.

Morahan et al., "Markers on distal chromosome 2q linked to insulin-dependent diabetes melliuts," *Science*, 272: 1811-1813, 1996.

Morkve et al., "Prognostic significance of p53 protein expression and DNA ploidy in surgically treated non-small cell lung carcinomas," *Anticancer Research*, 13(3): 571-578, 1993.

Muguerza et al., "Prognostic value of flow cytometric DNA analysis in small-cell lung cancer: rationale of sequential processing of frozen and paraffin-embedded tissue," *World J. Surg.* 21(3): 323-329, 1997.

Naruke et al., "Prognosis and survival in resected lung carcinoma based on the new international staging system," *J. Thorac. Cardiovas. Surg.*, 96:440-447, 1988.

Nastiuk et al., "Common mutations in BRCA1 and BRCA2 do not contribute to early prostate cancer in Jewish men," *The Prostate*, 40:172-77, 1999.

Nelen et al., "Germline mutations in the PTEN/MMAC1 gene in patients with Cowden disease," *Human Mol. Genetics*, 6(8):1383-1387, 1997.

O'Reilly et al., "Differential effects of glucocorticoid on expression of surfactant proteins in a human lung adenocarcinoma cell line," *Biochim. Biophys. Acta*, 970:194-204, 1988.

Office Action, issued in U.S. Appl. No. 09/923,304, mailed Apr. 19, 2002.

Office Action, issued in U.S. Appl. No. 09/923,304, mailed Jul. 18, 2002.

Office Action, issued in U.S. Appl. No. 09/923,304, mailed Apr. 8, 2003.

Office Action, issued in U.S. Appl. No. 09/923,304, mailed Jan. 13, 2004.

Office Action, issued in U.S. Appl. No. 10/952,251, mailed Dec. 22, 2006.

Office Action, issued in U.S. Appl. No. 10/952,251, mailed Sep. 5, 2007.

Office Action, issued in U.S. Appl. No. 10/952,251, mailed Dec. 19, 2007.

Office Action, issued in U.S. Appl. No. 10/952,251, mailed Oct. 3, 2008.

Office Action, issued in U.S. Appl. No. 10/952,251, mailed Apr. 15, 2009.

Okada et al., "Isolation of human nm23 genomes and analysis of loss of heterozygosity in primary colorectal carcinomas using a specific genomic probe," *Cancer Research*, 54:3979-82, 1994.

Otto, "Lung epithelial stem cells," *J. Pathol.*, 197:527-535, 2002.

Pantel et al., "Expression of Lewis Y blood group precursor antigens on non-small cell lung carcinomas is associated with an unfavorable prognosis," *Proc. Annu Mt. Am. Soc. Clin. Oncol.*, 12:290, abstract # 941, 1993.

Papadimitrakopoulou et al., "Molecular and cellular biomarkers for field cancerization and multistep process in head and neck tumorigenesis," *Cancer and Metastasis Reviews*, 15: 53-76, 1996.

Pauletti et al., "Assessment of methods for tissue-based detection of the HER-2/neu alteration in human breast cancer: a direct comparison of fluorescence in situ hybridization and immunohistochemistry," *J. Clinical Oncology*, 18:3651-3664, 2000.

PCT International Search Report and Written Opinion, issued in International Application No. PCT/US2007/061073, dated Aug. 9, 2007.

Pence et al., "Prognostic significance of the proliferation index in surgically resected non-small-cell lung cancer," *Archives of Surgery*, 128(12): 1382-1390, 1993.

Peterson et al., "Distinct regions of allelic imbalance on chromosome 10q22-q26 in squamous cell carcinomas of the lung," *Oncogene*, 17:449-454, 1998.

Qi et al., "Isolation of novel differentially expressed genes related to human glioma using cDNA microarray and characerizations of two novel full-length genes," *J of Neuro-Oncology*, 53:197-208, 2002.

Rice et al., "Prognostic significance of flow cytometry in non-small-cell lung cancer," *J. Thoracic Cardio. Surgery*, 106(2): 201-217, 1993.

Romeo et al., "Chromosomal abnormalitites in non-small cell lung carcinomas and in bronchial epithelia of high-risk smokers detected by multi-target interphase fluorescence in situ hybridization," *J. Mol. Diagnostics*, 5:103-112, 2003.

Sahin et al., "Flow cytometric analysis of the DNA content of non-small-cell lung cancer. Ploidy as a significant prognostic indicator in squamous cell carcinoma of the lung," *Cancer*, 65(3): 530-537, 1990.

Sanchez-Cespedes et al., "Increased loss of chromosome 9p21 but not *p16* inactivation in primary non-small cell lung cancer from smokers," *Cancer Res*, 61:2092-2096, 2001.

Scully et al., "Genetic aberrations in oral or head and neck squamous cell carcinoma 2: chromosomal aberrations," *Oral Oncology*, 36:311-327, 2000.

Shijubo et al., "Pulmonary surfactant protein A in pleural effusions," *Cancer*, 69:2905-2909, 1992.

Shiseki et al., "Comparative allelotype of early and advanced stage non-small cell lung carcinomas," *Genes Chromosomes Cancer*, 17(2): 71-77, 1996.

Shriver et al., "Trinucleotide repeat length variation in the human ribosomal protein L14 gene (RPL14): localization to 3p21.3 and loss of heterozygosity in lung and oral cancers," *Mutat. Res.* 406(1): 9-23, 1998.

Sidransky et al., "Identification of p53 gene mutations in bladder cancers and urine samples," *Science*, 252: 706-709, 1991.

Siebert et al., "Detection of deletions in the short arm of chromosome 3 in uncultured renal cell carcinomas by interphase cytogenetics," *J. Urol.*, 160(2):534-539, 1998.

Slamon et al., "Studies of the HER-2/new proto-oncogene in human breast and ovarian cancer," *Science*, 244: 707-712, 1989.

Steck et al., "Identification of a candidate tumour suppressor gene, MMAC1, at chromosome 10q23.3 that is mutated in multiple advanced cancers," *Nature Genetics*, 15:356-362, 1997.

Tanaka et al. "Triple repeat-containing ribosomal protein L14 gene in immortalized human endothelial cell line," *Biochemical and Biophysical Research Communications*, 243:531-537, 1998.

Taparowsky et al, "Activation of the T24 bladder carcinoma transforming gene is linked to a single amino acid change," *Nature*, 300: 762-765, 1982.

Teng et al., "MMAC1/PTEN mutations in primary tumor specimens and tumor cell lines," *Cancer Research*, 57:5221-5225, 1997.

Thiberville et al, "Evidence of cumulative gene losses with progression of premalignant epithelial lesions to carcinoma of the bronchus," *Cancer Research*, 55: 5133-5139, 1995.

Thiberville et al., "Frequency and prognostic evaluation of 3p21-22 allelic losses in non-small-cell lung cancer," *Int. J. Cancer*, 64:371-377, 1995.

Travis et al., "Lung Cancer," *Cancer*, 75:191-202, 1995.

Tsutsumida et al., "Combined status of MUC1 mucin and surfactant apoprotein A expression can predict the outcome of patients with small-size lung adenocarcinoma," *Histopathology*, 44:147-155, 2004.

Valdivieso et al, "Clinical and molecular markers of prognosis in non-small cell lung cancer (NSCLC)," *Proc. Annu. Mt. Am. Soc. Clin. Oncol.*, 13:337, abstract # 1121, 1994.

Varella-Garcia et al., "Multi-target interphase fluorescence in situ hybridization assay increases sensitivity of sputum cytology as a predictor of lung cancer," *Cancer Detection and Prevention*, 28:244-251, 2004.

Virmani et al., "Comparison between fluorescence in situ hybridization and classical cytogenetics in human tumors," *Anticancer Research*, 18:1351-1356, 1998.

Vollmer et al., "Subclassification of small cell cancer of the lung," The Southeastern Study Group Experience, *Hum Pathol*, 16:247-252, 1985.

Volm et al., "Prognostic significance of DNA ploidy and distribution of cell cycle phases in non-small cell bronchial cancer," *Versicherungsmedizin*, 41(1): 2-5, 1989, Article in German, English abstract included.

Voravud, et al., "Increased polysomies of chromosomes 7 and 17 during head and neck multistage tumorigenesis," *Cancer Research*, 53: 2874-2883, 1993.

Wang et al., "Overexpression of S100A2 protein as a prognostic marker for patients with stage I non small cell lung cancer," *International Journal of Cancer*, 116:285-290, 2005.

Whang-Peng et al., "A nonrandom chromosomal abnormality, del 3p(14-23), in human small cell lung cancer (SCLC)," *Cancer Genet. Cytogenet.*, 6(2):119-134, 1982.

Wiest et al., "Genetic markers for early detection of lung cancer and outcome measures for response to chemoprevention," *J. Cell Biochem. Suppl.*, 28/29:64-73, 1997.

Wiest et al., "Identification of a novel region of homozygous deletion on chromosome 9p in squamous cell carcinoma of the lung: the location of a putative tumor suppressor gene," *Cancer Res*, 57:1-6, 1997.

Winston et al., "HER-2/neu evaluation in breast cancer are we there yet?," *Amer. J Clinical. Pathology*, 121:S33-49, 2004.

Wistuba et al., "High resolution chromosome 3p allelotyping of human lung cancer and preneoplastic/preinvasive bronchial epithelium reveals multiple, discontinuous sites of 3p allele loss and three regions of frequent breakpoints," *Cancer Res.*, 60(7): 1949-1960, 2000.

Wu et al., "Benzo[a]pyrene diol epoxide-induced 3p21.3 aberrations and genetic predisposition to lung cancer," *Cancer Res.*, 58(8): 1605-1608, 1998.

Wu et al., "Chromosome 5 aberrations and genetic predisposition to lung cancer," *Int J. Cancer*, 79(5):490-493, 1998.

Yamaoka et al., "The prognostic significance of nuclear DNA content in non-small-cell lung carcinoma," *J. Japan Surgical Soc.*, 91(10): 1608-1616, 1990, Article in Japanese, English abstract included.

Yanagisawa et al., "Molecular analysis of the FHIT gene at 3p14.2 in lung cancer cell lines," *Cancer Research*, 56: 5579-5582, 1996.

Zamecnik and Kodet, "Value of thyroid transcription factor-1 and surfactant apoprotein A in the differential diagnosis of pulmonary carcinomas: a study of 109 cases," *Virchows Archiv.*, 440:353-361, 2002.

Zani et al., "Molecular cloning of complex chromosomal translocation t(8;14;12)(q24.1;q32.3;q24.1) in a Burkitt lymphoma cell line defines a new gene (BCL7A) with homology to caldesmon," *Blood*, 87:3124-3134, 1996.

Zhu et al., "A case-control analysis of lymphocytic chromosome 9 aberrations in lung cancer," *Int. J. Cancer*, 102:536-540, 2002.

Zou et al., "Higher potency of N-(4-Hydroxyphenyl)retinamide that all-trans-retinoic acid in induction of apoptosis in non-small cell lung cancer cell lines," *Clinical Cancer Research* 4: 1345-1355, 1998.

\* cited by examiner

Relapse Status

Relapse Status

SEQUENCE LISTING

<160> NUMBER OF SEQ ID NOS: 11

<210> SEQ ID NO 1
<211> LENGTH: 722
<212> TYPE: DNA
<213> ORGANISM: Homo sapiens
<220> FEATURE:
<221> NAME/KEY: CDS
<222> LOCATION: (18)..(680)

<400> SEQUENCE: 1

```
cgcctaacgc tgccaac atg gtg ttc agg cgc ttc gtg gag gtt ggc cgg         50
                   Met Val Phe Arg Arg Phe Val Glu Val Gly Arg
                    1               5                  10 gtg gcc tat gtc tcc ttt gga cct cat gcc gga aaa ttg gtc gcg att         98
Val Ala Tyr Val Ser Phe Gly Pro His Ala Gly Lys Leu Val Ala Ile
            15                  20                  25 gta gat gtt att gat cag aac agg gct ttg gtc gat gga cct tgc act        146
Val Asp Val Ile Asp Gln Asn Arg Ala Leu Val Asp Gly Pro Cys Thr
        30                  35                  40 caa gtg agg aga cag gcc atg cct ttc aag tgc atg cag ctc act gat        194
Gln Val Arg Arg Gln Ala Met Pro Phe Lys Cys Met Gln Leu Thr Asp
    45                  50                  55 ttc atc ctc aag ttt ctg cac agt gcc cac cag aag tat gtc cga caa        242
Phe Ile Leu Lys Phe Leu His Ser Ala His Gln Lys Tyr Val Arg Gln
 60                  65                  70                  75 gcc tgg cag aag gca gac atc aat aca aaa tgg gca gcc aca cga tgg        290
Ala Trp Gln Lys Ala Asp Ile Asn Thr Lys Trp Ala Ala Thr Arg Trp
                 80                  85                  90 gcc aag aag att gaa gcc aga gaa agg aaa gcc aag atg aca gat ttt        338
Ala Lys Lys Ile Glu Ala Arg Glu Arg Lys Ala Lys Met Thr Asp Phe
             95                 100                 105 gat cgt ttt aaa gtt atg aag gca aag aaa atg agg aac aga ata atc        386
Asp Arg Phe Lys Val Met Lys Ala Lys Lys Met Arg Asn Arg Ile Ile
        110                 115                 120 aag aat gaa gtt aag aag ctt caa aag gca gct ctc ctg aaa gct tct        434
Lys Asn Glu Val Lys Lys Leu Gln Lys Ala Ala Leu Leu Lys Ala Ser
    125                 130                 135 ccc aaa aaa gca cct ggt act aag ggt act gct gct gct gct gct gct        482
Pro Lys Lys Ala Pro Gly Thr Lys Gly Thr Ala Ala Ala Ala Ala Ala
140                 145                 150                 155 gct gct gct gct gct gct gct gct aaa gtt cca gca aaa aag atc             530
Ala Ala Ala Ala Ala Ala Ala Ala Lys Val Pro Ala Lys Lys Ile
                160                 165                 170 acc gcc gcg agt aaa aag gct cca gcc cag aag gtt cct gcc cag aaa        578
Thr Ala Ala Ser Lys Lys Ala Pro Ala Gln Lys Val Pro Ala Gln Lys
                175                 180                 185 gcc aca ggc cag aaa gca gcg cct gct cca aaa gct cag aag ggt caa        626
Ala Thr Gly Gln Lys Ala Ala Pro Ala Pro Lys Ala Gln Lys Gly Gln
                190                 195                 200 aaa gct cca gcc cag aaa gca cct gct cca aag gca tct ggc aag aaa        674
Lys Ala Pro Ala Gln Lys Ala Pro Ala Pro Lys Ala Ser Gly Lys Lys
    205                 210                 215 gca taa gtggcaatca taaaaagtaa taaggttct ttttgacctg tt                  722
Ala
220
```

<210> SEQ ID NO 2
<211> LENGTH: 220
<212> TYPE: PRT
<213> ORGANISM: Homo sapiens

<400> SEQUENCE: 2

```
Met Val Phe Arg Arg Phe Val Glu Val Gly Arg Val Ala Tyr Val Ser
 1               5                  10                  15

Phe Gly Pro His Ala Gly Lys Leu Val Ala Ile Val Asp Val Ile Asp
             20                  25                  30

Gln Asn Arg Ala Leu Val Asp Gly Pro Cys Thr Gln Val Arg Arg Gln
         35                  40                  45

Ala Met Pro Phe Lys Cys Met Gln Leu Thr Asp Phe Ile Leu Lys Phe
     50                  55                  60

Leu His Ser Ala His Gln Lys Tyr Val Arg Gln Ala Trp Gln Lys Ala
 65                  70                  75                  80

Asp Ile Asn Thr Lys Trp Ala Ala Thr Arg Trp Ala Lys Lys Ile Glu
                 85                  90                  95

Ala Arg Glu Arg Lys Ala Lys Met Thr Asp Phe Asp Arg Phe Lys Val
            100                 105                 110

Met Lys Ala Lys Lys Met Arg Asn Arg Ile Ile Lys Asn Glu Val Lys
        115                 120                 125

Lys Leu Gln Lys Ala Ala Leu Leu Lys Ala Ser Pro Lys Lys Ala Pro
    130                 135                 140

Gly Thr Lys Gly Thr Ala Ala Ala Ala Ala Ala Ala Ala Ala Ala Ala
145                 150                 155                 160

Ala Ala Ala Ala Lys Val Pro Ala Lys Lys Ile Thr Ala Ala Ser Lys
                165                 170                 175

Lys Ala Pro Ala Gln Lys Val Pro Ala Gln Lys Ala Thr Gly Gln Lys
            180                 185                 190

Ala Ala Pro Ala Pro Lys Ala Gln Lys Gly Gln Lys Ala Pro Ala Gln
        195                 200                 205

Lys Ala Pro Ala Pro Lys Ala Ser Gly Lys Lys Ala
    210                 215                 220
```

<210> SEQ ID NO 3
<211> LENGTH: 2797
<212> TYPE: DNA
<213> ORGANISM: Homo sapiens
<220> FEATURE:
<221> NAME/KEY: CDS
<222> LOCATION: (83)..(1672)

<400> SEQUENCE: 3

```
acccacgcgt ctggccgcgg gccgcctctg cggcagcgct agtcgccttc tccgaatcgg      60
ctccgcacag ctaggagaaa ag atg ttc act gtg ctg acc cgc caa cca tgt     112
                         Met Phe Thr Val Leu Thr Arg Gln Pro Cys
                          1               5                  10 gag caa gca ggc ctc aag gcc ctc tac cga act cca acc atc att gcc     160
Glu Gln Ala Gly Leu Lys Ala Leu Tyr Arg Thr Pro Thr Ile Ile Ala
             15                  20                  25 ttg gtg gtc ttg ctt gtg agt att gtg gta ctt gtg agt atc act gtc     208
Leu Val Val Leu Leu Val Ser Ile Val Val Leu Val Ser Ile Thr Val
         30                  35                  40 atc cag atc cac aag caa gag gtc ctc cct cca gga ctg aag tat ggt     256
Ile Gln Ile His Lys Gln Glu Val Leu Pro Pro Gly Leu Lys Tyr Gly
     45                  50                  55 att gtg ctg gat gcc ggg tct tca aga acc aca gtc tac gtg tat caa     304
Ile Val Leu Asp Ala Gly Ser Ser Arg Thr Thr Val Tyr Val Tyr Gln
 60                  65                  70 tgg cca gca gaa aaa gag aat aat acc gga gtg gtc agt caa acc ttc     352
Trp Pro Ala Glu Lys Glu Asn Asn Thr Gly Val Val Ser Gln Thr Phe
```

|    |    |    |    |    |    |    |    |    |    |    |    |    |    |    |    |      |
|----|----|----|----|----|----|----|----|----|----|----|----|----|----|----|----|------|
|    | 75 |    |    |    | 80 |    |    |    | 85 |    |    |    | 90 |    |    |      |
| aaa | tgt | agt | gtg | aaa | ggc | tct | gga | atc | tcc | agc | tat | gga | aat | aac | ccc | 400  |
| Lys | Cys | Ser | Val | Lys | Gly | Ser | Gly | Ile | Ser | Ser | Tyr | Gly | Asn | Asn | Pro |      |
|     |     |     |     | 95  |     |     |     |     | 100 |     |     |     |     | 105 |     |      |
| caa | gat | gtc | ccc | aga | gcc | ttt | gag | gag | tgt | atg | caa | aaa | gtc | aag | ggg | 448  |
| Gln | Asp | Val | Pro | Arg | Ala | Phe | Glu | Glu | Cys | Met | Gln | Lys | Val | Lys | Gly |      |
|     |     |     | 110 |     |     |     |     | 115 |     |     |     |     | 120 |     |     |      |
| cag | gtt | cca | tcc | cac | ctc | cac | gga | tcc | acc | ccc | att | cac | ctg | gga | gcc | 496  |
| Gln | Val | Pro | Ser | His | Leu | His | Gly | Ser | Thr | Pro | Ile | His | Leu | Gly | Ala |      |
|     |     |     | 125 |     |     |     |     | 130 |     |     |     |     | 135 |     |     |      |
| acg | gct | ggg | atg | cgc | ttg | ctg | agg | ttg | caa | aat | gaa | aca | gca | gct | aat | 544  |
| Thr | Ala | Gly | Met | Arg | Leu | Leu | Arg | Leu | Gln | Asn | Glu | Thr | Ala | Ala | Asn |      |
|     |     | 140 |     |     |     |     | 145 |     |     |     |     | 150 |     |     |     |      |
| gaa | gtc | ctt | gaa | agc | atc | caa | agc | tac | ttc | aag | tcc | cag | ccc | ttt | gac | 592  |
| Glu | Val | Leu | Glu | Ser | Ile | Gln | Ser | Tyr | Phe | Lys | Ser | Gln | Pro | Phe | Asp |      |
| 155 |     |     |     |     | 160 |     |     |     |     | 165 |     |     |     |     | 170 |      |
| ttt | agg | ggt | gct | caa | atc | att | tct | ggg | caa | gaa | gaa | ggg | gta | tat | gga | 640  |
| Phe | Arg | Gly | Ala | Gln | Ile | Ile | Ser | Gly | Gln | Glu | Glu | Gly | Val | Tyr | Gly |      |
|     |     |     |     | 175 |     |     |     |     | 180 |     |     |     |     | 185 |     |      |
| tgg | att | aca | gcc | aac | tat | tta | atg | gga | aat | ttc | ctg | gag | aag | aac | ctg | 688  |
| Trp | Ile | Thr | Ala | Asn | Tyr | Leu | Met | Gly | Asn | Phe | Leu | Glu | Lys | Asn | Leu |      |
|     |     |     | 190 |     |     |     |     | 195 |     |     |     |     | 200 |     |     |      |
| tgg | cac | atg | tgg | gtg | cac | ccg | cat | gga | gtg | gaa | acc | acg | ggt | gcc | ctg | 736  |
| Trp | His | Met | Trp | Val | His | Pro | His | Gly | Val | Glu | Thr | Thr | Gly | Ala | Leu |      |
|     |     | 205 |     |     |     |     | 210 |     |     |     |     | 215 |     |     |     |      |
| gac | tta | ggt | ggt | gcc | tcc | acc | caa | ata | tcc | ttc | gtg | gca | gga | gag | aag | 784  |
| Asp | Leu | Gly | Gly | Ala | Ser | Thr | Gln | Ile | Ser | Phe | Val | Ala | Gly | Glu | Lys |      |
|     | 220 |     |     |     |     | 225 |     |     |     |     | 230 |     |     |     |     |      |
| atg | gat | ctg | aac | acc | agc | gac | atc | atg | cag | gtg | tcc | ctg | tat | ggc | tac | 832  |
| Met | Asp | Leu | Asn | Thr | Ser | Asp | Ile | Met | Gln | Val | Ser | Leu | Tyr | Gly | Tyr |      |
| 235 |     |     |     | 240 |     |     |     |     | 245 |     |     |     |     | 250 |     |      |
| gta | tac | acg | ctc | tac | aca | cac | agc | ttc | cag | tgc | tat | ggc | cgg | aat | gag | 880  |
| Val | Tyr | Thr | Leu | Tyr | Thr | His | Ser | Phe | Gln | Cys | Tyr | Gly | Arg | Asn | Glu |      |
|     |     |     |     | 255 |     |     |     |     | 260 |     |     |     |     | 265 |     |      |
| gct | gag | aag | aag | ttt | ctg | gca | atg | ctc | ctg | cag | aat | tct | cct | acc | aaa | 928  |
| Ala | Glu | Lys | Lys | Phe | Leu | Ala | Met | Leu | Leu | Gln | Asn | Ser | Pro | Thr | Lys |      |
|     |     | 270 |     |     |     |     | 275 |     |     |     |     | 280 |     |     |     |      |
| aac | cat | ctc | acc | aat | ccc | tgt | tac | cct | cgg | gat | tat | agc | atc | agc | ttc | 976  |
| Asn | His | Leu | Thr | Asn | Pro | Cys | Tyr | Pro | Arg | Asp | Tyr | Ser | Ile | Ser | Phe |      |
|     |     | 285 |     |     |     |     | 290 |     |     |     |     | 295 |     |     |     |      |
| acc | atg | ggc | cat | gta | ttt | gat | agc | ctg | tgc | act | gtg | gac | cag | agg | cca | 1024 |
| Thr | Met | Gly | His | Val | Phe | Asp | Ser | Leu | Cys | Thr | Val | Asp | Gln | Arg | Pro |      |
|     | 300 |     |     |     |     | 305 |     |     |     |     | 310 |     |     |     |     |      |
| gaa | agt | tat | aac | ccc | aat | gat | gtc | atc | act | ttt | gaa | gga | act | ggg | gac | 1072 |
| Glu | Ser | Tyr | Asn | Pro | Asn | Asp | Val | Ile | Thr | Phe | Glu | Gly | Thr | Gly | Asp |      |
| 315 |     |     |     | 320 |     |     |     |     | 325 |     |     |     |     | 330 |     |      |
| cca | tct | ctg | tgt | aag | gag | aag | gtg | gct | tcc | ata | ttt | gac | ttc | aaa | gct | 1120 |
| Pro | Ser | Leu | Cys | Lys | Glu | Lys | Val | Ala | Ser | Ile | Phe | Asp | Phe | Lys | Ala |      |
|     |     |     |     | 335 |     |     |     |     | 340 |     |     |     |     | 345 |     |      |
| tgc | cat | gat | caa | gaa | acc | tgt | tct | ttt | gat | ggg | gtt | tat | cag | cca | aag | 1168 |
| Cys | His | Asp | Gln | Glu | Thr | Cys | Ser | Phe | Asp | Gly | Val | Tyr | Gln | Pro | Lys |      |
|     |     |     | 350 |     |     |     |     | 355 |     |     |     |     | 360 |     |     |      |
| att | aaa | ggg | cca | ttt | gtg | gct | ttt | gca | gga | ttc | tac | tac | aca | gcc | agt | 1216 |
| Ile | Lys | Gly | Pro | Phe | Val | Ala | Phe | Ala | Gly | Phe | Tyr | Tyr | Thr | Ala | Ser |      |
|     |     | 365 |     |     |     |     | 370 |     |     |     |     | 375 |     |     |     |      |
| gct | tta | aat | ctt | tca | ggt | agc | ttt | tcc | ctg | gac | acc | ttc | aac | tcc | agc | 1264 |
| Ala | Leu | Asn | Leu | Ser | Gly | Ser | Phe | Ser | Leu | Asp | Thr | Phe | Asn | Ser | Ser |      |
|     | 380 |     |     |     |     | 385 |     |     |     |     | 390 |     |     |     |     |      |
| acc | tgg | aat | ttc | tgc | tca | cag | aat | tgg | agt | cag | ctc | cca | ctg | ctg | ctc | 1312 |
| Thr | Trp | Asn | Phe | Cys | Ser | Gln | Asn | Trp | Ser | Gln | Leu | Pro | Leu | Leu | Leu |      |

```
                     395                 400                 405                 410
ccc aaa ttt gat gag gta tat gcc cgc tct tac tgc ttc tca gcc aac    1360
Pro Lys Phe Asp Glu Val Tyr Ala Arg Ser Tyr Cys Phe Ser Ala Asn
                         415                 420                 425 tac atc tac cac ttg ttt gtg aac ggt tac aaa ttc aca gag gag act    1408
Tyr Ile Tyr His Leu Phe Val Asn Gly Tyr Lys Phe Thr Glu Glu Thr
                 430                 435                 440 tgg ccc caa ata cac ttt gaa aaa gaa gtg ggg aat agc agc ata gcc    1456
Trp Pro Gln Ile His Phe Glu Lys Glu Val Gly Asn Ser Ser Ile Ala
             445                 450                 455 tgg tct ctt ggc tac atg ctc agc ctg acc aac cag atc cca gct gaa    1504
Trp Ser Leu Gly Tyr Met Leu Ser Leu Thr Asn Gln Ile Pro Ala Glu
         460                 465                 470 agc cct ctg atc cgt ctg ccc ata gaa cca cct gtc ttt gtg ggc acc    1552
Ser Pro Leu Ile Arg Leu Pro Ile Glu Pro Pro Val Phe Val Gly Thr
475                 480                 485                 490 ctc gct ttc ttc aca gtg gca gcc ttg ctg tgt ctg gca ttt ctt gca    1600
Leu Ala Phe Phe Thr Val Ala Ala Leu Leu Cys Leu Ala Phe Leu Ala
                     495                 500                 505 tac ctg tgt tca gca acc aga aga aag agg cac tcc gag cat gcc ttt    1648
Tyr Leu Cys Ser Ala Thr Arg Arg Lys Arg His Ser Glu His Ala Phe
                 510                 515                 520 gac cat gca gtg gat tct gac tga gccttcaaag cagctcctgg agtccaatgg   1702
Asp His Ala Val Asp Ser Asp
             525 ctgcttagag tcagcctggg tggcaccagg caatgcaggt gaagtggctg ccttcaggaa   1762
atacaactaa ctaaaatcaa acacctaggt cacgtgcctc tcaaatactg atttctgcca   1822
cagcacctct tgaggcatcc cttggctatt ctgtgcatat tgttcttcag agacctcact   1882
acccacatgc tgatctattg gggaacagag aagagacagg ccactaaggt caggctcttt   1942
atattaagtt ccccagagga agagtaagtt gagaaggtat cagtttaatg ttgaagaatt   2002
gacctcaggg ctcagtttcc atttccctcc ctcagtattc ttcctggcaa gatacccatt   2062
aagcatttcg ccaatcagaa tctcatttta tagttttttcc cattggtctt taactaagac   2122
tttcttgtag caatctcgta agcagtgaac cccctcagat cagtagaata tagtatctgg   2182
gggagaagac ttacttcctt cagggcagca gccacagcca ggcttctgtc atacaggtag   2242
atcccgaagc acagagacat aaaaaaggtc tcccagaaaa ctatagacca ttctccaagt   2302
ggaattccca cttagggctc tggtcactag attgcaacct gtgtgtttgt catcatcctc   2362
atctcaccat tgtattgcta tgccctccca taaaaacaca ttgatcccta gcaagattat   2422
tgcattccag attttactgc ctttgctagg cttttgctta gcaaagggct gactttccat   2482
tgttatcatg gtgtatatat ttttgtcacc attcccacaa gtatacttga tgttgtcata   2542
gaacgaacat cctactctat gatttactaa ccaattactt tcccagatca tagacctctc   2602
tgcatagtag tcataggtct tgactttggg gaaagaaaag gaagctgcag gaatatttat   2662
ctccaaagtc gaatgagaaa gaactccagc aaatccaatg gctacaaact aaaaatcagc   2722
attatttcat attgctgttt cttagctgaa tatggaataa agaactatta ttttatttg   2782
aaaaaaaaaa aaaaa                                                    2797

<210> SEQ ID NO 4
<211> LENGTH: 529
<212> TYPE: PRT
<213> ORGANISM: Homo sapiens

<400> SEQUENCE: 4
```

-continued

```
Met Phe Thr Val Leu Thr Arg Gln Pro Cys Glu Gln Ala Gly Leu Lys
 1               5                  10                  15

Ala Leu Tyr Arg Thr Pro Thr Ile Ile Ala Leu Val Val Leu Leu Val
                20                  25                  30

Ser Ile Val Val Leu Val Ser Thr Val Ile Gln Ile His Lys Gln
            35                  40                  45

Glu Val Leu Pro Pro Gly Leu Lys Tyr Gly Ile Val Leu Asp Ala Gly
        50                  55                  60

Ser Ser Arg Thr Thr Val Tyr Val Tyr Gln Trp Pro Ala Glu Lys Glu
 65                  70                  75                  80

Asn Asn Thr Gly Val Val Ser Gln Thr Phe Lys Cys Ser Val Lys Gly
                    85                  90                  95

Ser Gly Ile Ser Ser Tyr Gly Asn Asn Pro Gln Asp Val Pro Arg Ala
                100                 105                 110

Phe Glu Glu Cys Met Gln Lys Val Lys Gly Gln Val Pro Ser His Leu
                115                 120                 125

His Gly Ser Thr Pro Ile His Leu Gly Ala Thr Ala Gly Met Arg Leu
    130                 135                 140

Leu Arg Leu Gln Asn Glu Thr Ala Ala Asn Glu Val Leu Glu Ser Ile
145                 150                 155                 160

Gln Ser Tyr Phe Lys Ser Gln Pro Phe Asp Phe Arg Gly Ala Gln Ile
                165                 170                 175

Ile Ser Gly Gln Glu Glu Gly Val Tyr Gly Trp Ile Thr Ala Asn Tyr
                180                 185                 190

Leu Met Gly Asn Phe Leu Glu Lys Asn Leu Trp His Met Trp Val His
                195                 200                 205

Pro His Gly Val Glu Thr Thr Gly Ala Leu Asp Leu Gly Gly Ala Ser
    210                 215                 220

Thr Gln Ile Ser Phe Val Ala Gly Glu Lys Met Asp Leu Asn Thr Ser
225                 230                 235                 240

Asp Ile Met Gln Val Ser Leu Tyr Gly Tyr Val Tyr Thr Leu Tyr Thr
                245                 250                 255

His Ser Phe Gln Cys Tyr Gly Arg Asn Glu Ala Glu Lys Lys Phe Leu
                260                 265                 270

Ala Met Leu Leu Gln Asn Ser Pro Thr Lys Asn His Leu Thr Asn Pro
                275                 280                 285

Cys Tyr Pro Arg Asp Tyr Ser Ile Ser Phe Thr Met Gly His Val Phe
                290                 295                 300

Asp Ser Leu Cys Thr Val Asp Gln Arg Pro Glu Ser Tyr Asn Pro Asn
305                 310                 315                 320

Asp Val Ile Thr Phe Glu Gly Thr Gly Asp Pro Ser Leu Cys Lys Glu
                325                 330                 335

Lys Val Ala Ser Ile Phe Asp Phe Lys Ala Cys His Asp Gln Glu Thr
                340                 345                 350

Cys Ser Phe Asp Gly Val Tyr Gln Pro Lys Ile Lys Gly Pro Phe Val
                355                 360                 365

Ala Phe Ala Gly Phe Tyr Tyr Thr Ala Ser Ala Leu Asn Leu Ser Gly
    370                 375                 380

Ser Phe Ser Leu Asp Thr Phe Asn Ser Ser Thr Trp Asn Phe Cys Ser
385                 390                 395                 400

Gln Asn Trp Ser Gln Leu Pro Leu Leu Pro Lys Phe Asp Glu Val
                405                 410                 415

Tyr Ala Arg Ser Tyr Cys Phe Ser Ala Asn Tyr Ile Tyr His Leu Phe
                420                 425                 430
```

Val Asn Gly Tyr Lys Phe Thr Glu Glu Thr Trp Pro Gln Ile His Phe
        435                 440                 445

Glu Lys Glu Val Gly Asn Ser Ser Ile Ala Trp Ser Leu Gly Tyr Met
    450                 455                 460

Leu Ser Leu Thr Asn Gln Ile Pro Ala Glu Ser Pro Leu Ile Arg Leu
465                 470                 475                 480

Pro Ile Glu Pro Pro Val Phe Val Gly Thr Leu Ala Phe Phe Thr Val
                485                 490                 495

Ala Ala Leu Leu Cys Leu Ala Phe Leu Ala Tyr Leu Cys Ser Ala Thr
                500                 505                 510

Arg Arg Lys Arg His Ser Glu His Ala Phe Asp His Ala Val Asp Ser
            515                 520                 525

Asp

<210> SEQ ID NO 5
<211> LENGTH: 3771
<212> TYPE: DNA
<213> ORGANISM: Homo sapiens
<220> FEATURE:
<221> NAME/KEY: prim_transcript
<222> LOCATION: (921)..(3751)

<400> SEQUENCE: 5

```
ccatggcccc ttcattaggg ccccaattgt gactttattg ctcatagtct cttccctgcc      60
ttggtggctc tcatccccca aacctgaatg cagaagtctt ggtcctagac tcaactccgt     120 gccaccttc agcctacgtt gtgggttcct gctaagctga gcatttacct aacaatcaag     180
acttctgaca gtcctcagtc ctgccccaa acccccttgg atttctcttt ttcaaggtgg     240
tttcggctag gagagtgagc gtggcttggg tgagggcaga tagggtggga gcatgggca     300 tgtatggatg agaccttgac aaagggaccc cggaggaaag acaggggccc tttccccctt     360
tgtcctggaa acccggctca gccccagccc ttgcccattc tgctgctgct gcctggtacc     420
ttccacaagg ccagactcct ctccacaaag ctgtggtctg caccagctcc tctggctctc     480
ctcctctgcc tgctgagggc cgcctcctag cctggctgcc aatcacagga gaaagggtt     540 gggattttgt ttgtgcctct gtctgagcag agaatggctg ataggcactg agcgttgccc     600
tggagagccc ctctgtccct gctatcccca tctcccctgg cccagacttc tgcccttcac     660
gcccatccct gaccagcagc ccactcagt ctgggctctg ggtgccagct gtatagacat     720
gccacctgaa cccaggccag agctggtgat gcgtggggct atttttaagca cagcctcttg     780 gcctgcacac tccctggcc cccagcccc agcagctcag ctactggtca cctgccaccg     840 cctgaatgc tgattggcag ttggctgggg tgggtggggg ctgggaagac actattataa     900
agctgggagt gttgggaagc agccgtcccc gtccagagtc ctctgtggtc cctgctgcca     960
ccatggccac tcaccgcctc gtgatggtcc ggcacggcga gagcacatgg aaccaggaga    1020
accgtttctg tggctggttc gatgcagagc tgagtgaaaa ggggaccgag gaggccaagc    1080
ggggagccaa ggccatcaag gatgccaaga tggagtttga catctgctac acgtcagtgc    1140
tgaagcgggc catcccgacc ctctgggcca tcctggacgg cacggaccag atgtggctgc    1200
ctgtggtgcg cacttgccgc ttcaatgagc ggcattacgg gggcctcaca ggcctcaaca    1260
aggcagaaac ggccgccaag cacggggagg agcaggtgaa gatctggagg cgctccttcg    1320
acatcccgcc gccccgatg gacgagaagc cccctacta caactccatt agcaaggtgg    1380
gctgcctttg ctgggaaggc ctctgggaag ctgcagagtg gggagtcggg tgggggccca    1440
```

```
ctggcttggg agggaaagca gcgtgcctgt gtcccccagg agcgtcggta cgcaggcctg    1500
aagcccgggg aactcccac ctgcgagagc ctcaaggaca ccattgcccg ggccctgccc    1560
ttctggaacg aggagattgt tccccagatc aaggccggca agcgagtgct cattgcagcc    1620
cacgggaaca gcctgcgggg cattgtcaag cacctggaag gtaggccacc ttcaggagcc    1680
tgggcagggt gggtgggcag cagccagctg gcttctcatc tcagcaaagt ctctcgccat    1740
gaccagcttt ctagcgtggc tccacatcat tcactgaaaa gaggctgaga agccattttt    1800
tagttttgtg aaattttccc catttctgtg taactggaca cactccacag gggctgactg    1860
cactcgaagc tcgctgtgtc ccgaggtggg gcaggctcca aggtggcat ctgccaaggg    1920 acacccagct aggaaacgga agggctgggc ttagagcatc tggctccaaa tcccaactta    1980
ctgtggggcc ctggacaagc cacctccatc tctgggcctc tcccttttcc ggggtggtgg    2040
ggagctcccc ctggtactga attcctcttg atgtaggctt ggaccctcg cagggccctc    2100 ccccatcagg tcctcagaat ccctgcatga gcttcaccac ctatctccct ctggagcccc    2160
tctctgggca aggaaagac caatcaaaag aggggtgcag gactatggag tggccagact    2220
ctgggcttgc agctgggctc ccactgaaga gcaaggctg acaaatgggc ccggatgca    2280 tgggcgcagt aaggcctcgc ccagagtgac tggcacctcc gtccgcctcc caccttagta    2340
ttctgacaca agggcagtct aaattagcat ctgaatgacc ttaaagcttg ttgagtcctg    2400
gaaaggctag aagggtgtgc cccagacctc ctgctcctag ggccgttggg cagttggcca    2460
gagcacccag accggcaggc cccggagacc cagccagccc caagcctgcc cgctccaaac    2520
acggacacct ggcacctggc actggggcca ggcagaggga aggaccacct gcctcctctc    2580
ccttccggag acttcatgca gccccatgac cctcccacag cctggtttgg ggaaaggga    2640 cgcactttg gtggtgaata tgagggattt cactctgact ccccagagaa catttttctta    2700 aacccctccc tgcacggagc aggggtggag tggcgcgaac atcaaaggtc gagctgctat    2760
tcccagctca ggggctgcag gaggcaggca gggtcaggtt tcgaccaggc tcggcctccc    2820
tgtccctcct ccagctccat tccgcacttg ctcctctgtt caggatgtct agaatttaga    2880
gcactttaga aacaaagggt gctgggcacg gtggctcact cctgtaatcc cagcactttg    2940
ggaggctgag gcaggcagat cacctgaggt caggagtttg agaccagcct gaccaacatg    3000
gtaaaacccg tttctactaa aaatacaaaa ttagccgggt gtggtggcgc tcacctgtaa    3060
tcccagctac ttgggaggct gaggcagaat cacttcaacc caggagatgg aggttgcagt    3120
gagccaagat cgtgccactg cactccagcc tgggcaagag gagtaaaact ccatctcaaa    3180 aaaagaaaa agaaaagaa aagaaaaaa aaaccaaag ggtgagtgtc ccttcctgac    3240
cctcaacttc agtctggctg gagtcacact gggctgaggg aactatggac agcaccacca    3300
cagatcacag ccacttgggt ggggctgaag tccccatttt tttcaccact gggctatttc    3360
tgtaggctgc ttggtctaac tcagttactc cttgaccttt gcaacatttt ctgtggcctc    3420
gttctcaggg ctgggaagga attggtgcca ggggaactgg ctctgtggac cataaaggtc    3480
acatagtgtc tgctgtgtaa acaggctggg acagagggg ctaaggacac ctattccttc    3540
cggcataggg atgtcagacc aggcgatcat ggagctgaac ctgcccacgg ggatccccat    3600
tgtgtatgag ctgaacaagg agctgaagcc caccaagccc atgcagttcc tgggtgatga    3660
ggaaacggtg cggaaggcca tggaggctgt ggctgcccag ggcaaggcca agtgagggt    3720 gggcttgggc aataaaggca cctccccaa cagcctggag tctccagcgc a             3771
```

<210> SEQ ID NO 6

<211> LENGTH: 992
<212> TYPE: DNA
<213> ORGANISM: Homo sapiens
<220> FEATURE:
<221> NAME/KEY: CDS
<222> LOCATION: (242)..(583)

<400> SEQUENCE: 6

```
ttttgtgcga gagccgcagc gccgcctctt ctctcgcgcc ctcgcctctt cctccgcctc      60
ctccttcgcc tcttcctgcc tcctcccggc ttccgccgcc gccactccag cctaatccca     120
accccagggc gaaggttttc ttatttattt ccgttttctc gccactacag cctcctgaca     180
aggtgatccg ggcgggcccc gcaggaattt tatcccctca ccggcctcac actagtatcg     240
``` c atg tcc act atc cag aac ctc caa tct ttc gac ccc ttt gct gat gca       289
  Met Ser Thr Ile Gln Asn Leu Gln Ser Phe Asp Pro Phe Ala Asp Ala
  1               5                  10                  15 act aag ggt gac gac tta ctc ccg gca ggg act gag gat tac att cat         337
Thr Lys Gly Asp Asp Leu Leu Pro Ala Gly Thr Glu Asp Tyr Ile His
            20                  25                  30 ata aga atc cag caa cgg aac ggc aga aag aca ctg act act gtt cag         385
Ile Arg Ile Gln Gln Arg Asn Gly Arg Lys Thr Leu Thr Thr Val Gln
        35                  40                  45 ggc att gca gat gat tat gac aaa aag aaa ctt gtg aaa gct ttc aaa         433
Gly Ile Ala Asp Asp Tyr Asp Lys Lys Lys Leu Val Lys Ala Phe Lys
    50                  55                  60 aag aaa ttt gcc tgt aat ggt act gtg att gaa cat cct gaa tac gga         481
Lys Lys Phe Ala Cys Asn Gly Thr Val Ile Glu His Pro Glu Tyr Gly
65                  70                  75                  80 gag gtt att cag ctt caa ggt gac caa aga aaa aac atc tgc cag ttt         529
Glu Val Ile Gln Leu Gln Gly Asp Gln Arg Lys Asn Ile Cys Gln Phe
                85                  90                  95 ctc ttg gag gtt ggc att gta aag gag gaa cag ctt aag gtt cat gga         577
Leu Leu Glu Val Gly Ile Val Lys Glu Glu Gln Leu Lys Val His Gly
            100                 105                 110 ttc taa aatgaaccta aatacgtgga gaatttcttg aatagttttg ttctctaaac          633
Phe

```
ccggtttggc tgccttgtga aatgattccc tgcagtaaac ggacttttca tttatttaat      693
cattcaaact tccattcaca tctgcatgat tacagaaaac atggggtatg tagactagta      753
acacataaga aaattgcagt aagatggtaa caaaacctca tattgtcttt acatgtttcc      813
aatggaaaat gttttgagtg tttattgttc agtttattac gtttcacttg attaaatttt      873
ttttgttgtt gtattaaacc atgtacgttg cagcttaaca ataaaaaaaa aatctatgaa      933
tctttgtgag caattatgct cccaaatcta agcaagtaat aaagaagggg gattcaaag       992
```

<210> SEQ ID NO 7
<211> LENGTH: 113
<212> TYPE: PRT
<213> ORGANISM: Homo sapiens

<400> SEQUENCE: 7

Met Ser Thr Ile Gln Asn Leu Gln Ser Phe Asp Pro Phe Ala Asp Ala
1               5                  10                  15

Thr Lys Gly Asp Asp Leu Leu Pro Ala Gly Thr Glu Asp Tyr Ile His
            20                  25                  30

Ile Arg Ile Gln Gln Arg Asn Gly Arg Lys Thr Leu Thr Thr Val Gln
        35                  40                  45

Gly Ile Ala Asp Asp Tyr Asp Lys Lys Lys Leu Val Lys Ala Phe Lys
    50                  55                  60

```
Lys Lys Phe Ala Cys Asn Gly Thr Val Ile Glu His Pro Glu Tyr Gly
 65                  70                  75                  80

Glu Val Ile Gln Leu Gln Gly Asp Gln Arg Lys Asn Ile Cys Gln Phe
                 85                  90                  95

Leu Leu Glu Val Gly Ile Val Lys Glu Gln Leu Lys Val His Gly
            100                 105                 110

Phe
```

<210> SEQ ID NO 8
<211> LENGTH: 445
<212> TYPE: DNA
<213> ORGANISM: Homo sapiens

<400> SEQUENCE: 8

```
caccatgtcc actatccaga acctccaatc tttcgacccc tttgctgatg caactaaggg      60
tgacgactta ctcccggcag ggactgagga ttacattcat ataagaatcc agcaacggaa     120
cggcagaaag acactgacta ctgttcaggg cattgcagat gattatgaca aaagaaaact     180
tgtgaaagct ttcaaaaaga aatttgcctg taatggtact gtgattgaac atcctgaata     240
cggagaggtt attcagcttc aaggtgacca agaaaaaaac atctgccagt ttctcttgga     300
ggttggcatt gtaaaggagg aacagcttaa ggttcatgga ttcaagggcg agcttcgagg     360
tcacccattc gaaggtaagc ctatccctaa ccctctcctc ggtctcgatt ctacgcgtac     420
cggtcatcat caccatcacc attga                                           445
```

<210> SEQ ID NO 9
<211> LENGTH: 146
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

```
Met Ser Thr Ile Gln Asn Leu Gln Ser Phe Asp Pro Phe Ala Asp Ala
  1               5                  10                  15

Thr Lys Gly Asp Asp Leu Leu Pro Ala Gly Thr Glu Asp Tyr Ile His
                 20                  25                  30

Ile Arg Ile Gln Gln Arg Asn Gly Arg Lys Thr Leu Thr Thr Val Gln
             35                  40                  45

Gly Ile Ala Asp Asp Tyr Asp Lys Lys Lys Leu Val Lys Ala Phe Lys
         50                  55                  60

Lys Lys Phe Ala Cys Asn Gly Thr Val Ile Glu His Pro Glu Tyr Gly
 65                  70                  75                  80

Glu Val Ile Gln Leu Gln Gly Asp Gln Arg Lys Asn Ile Cys Gln Phe
                 85                  90                  95

Leu Leu Glu Val Gly Ile Val Lys Glu Gln Leu Lys Val His Gly
            100                 105                 110

Phe Lys Gly Glu Leu Arg Gly His Pro Phe Glu Gly Lys Pro Ile Pro
        115                 120                 125

Asn Pro Leu Leu Gly Leu Asp Ser Thr Arg Thr Gly His His His His
    130                 135                 140

His His
145
```

<210> SEQ ID NO 10
<211> LENGTH: 26
<212> TYPE: DNA

```
-continued

<213> ORGANISM: Artificial Sequence
<220> FEATURE:
<223> OTHER INFORMATION: Description of Artificial Sequence: Synthetic
      Primer

<400> SEQUENCE: 10
caccatgtcc actatccaga acctcc                                          26

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 11
gaatccatga accttaagct gttc                                            24
```

DETECTION AND DIAGNOSIS OF SMOKING RELATED CANCERS

The current application is a continuation of U.S. application Ser. No. 10/952,251, filed on Sep. 28, 2004, now U.S. Pat. No 7,741,034, which is a continuation of U.S. application Ser. No. 09/923,304, now U.S. Pat. No. 6,797,471, filed on Aug. 6, 2001 and claims priority to U.S. Provisional Application No. 60/222,811 filed Aug. 4, 2000. The entire text of each of the above-referenced disclosures is specifically incorporated by reference herein without disclaimer.

This invention was made with government support under contract number N01-CN-85184 pursuant to NCI, Dept. of Health and Human Services. The government has certain rights in the invention.

BACKGROUND OF THE INVENTION

1. Field of the Invention

The present invention relates to the fields of oncology, genetics and molecular biology. More particular the invention relates to the use of two probes for regions of human chromosomes 3 and 10 that are highly predictive of the development of neoplasia and progression of neoplastic events.

2. Related Art

Lung cancer is one of the leading causes of cancer death in the world. The high mortality rate for lung cancer probably results, at least in part, from the lack of standard clinical procedures for the diagnosis of the disease at early and more treatable stages compared to breast, prostate, and colon cancers. There is also extremely poor prognosis associated with diagnosis of the disease, especially in advanced disease. It is important that strategies to detect early stage lung carcinoma or its precursors, such as atypical squamous metaplasia, dysphasia and carcinoma-in-situ in subjects at high risk be devised.

Cigarette smoking over a prolonged period of time is the most important risk factor in the development of lung and other smoking related cancers, with other risk factors including exposure to passive smoking, certain industrial substances such as arsenic, some organic chemicals, radon and asbestosis, ingestion of alcohol, radiation exposure from occupational, medical and environmental sources, air pollution and tuberculosis. Many of these factors greatly increase the risk of development of lung and other smoking related cancers if they occur in a person who is concurrently a smoker.

Genetic detection of human disease states is a rapidly developing field (Taparowsky et al., 1982; Slamon et al., 1989; Sidransky et al., 1992; Miki et al., 1994; Dong et al., 1995; Morahan et al., 1996; Lifton, 1996; Barinaga, 1996). However, some problems exist with this approach. A number of known genetic lesions merely predispose to development of specific disease states. Individuals carrying the genetic lesion may not develop the disease state, while other individuals may develop the disease state without possessing a particular genetic lesion. In human cancers, genetic defects may potentially occur in a large number of known tumor suppresser genes and proto-oncogenes.

The genetic detection of cancer has a long history. One of the earliest genetic lesions shown to predispose to cancer was transforming point mutations in the ras oncogenes (Taparowsky et al., 1982). Deletion and mutation of p53 has been observed in bladder cancer (Sidransky et al., 1991). Numerous studies have shown deletions in the 3p region are related to lung and other smoking related cancers (Mitsudomi et al., 1996, Shiseki et al., 1996, Wistuba et al., 2000, Wu et al., 1998, and Shriver et al., 1998).

Molecular studies (fluorescence in situ hybridization (FISH) for polysomies, PCR for hypervariable markers (MI) and LOH, or specific mutations) have demonstrated that morphologically normal areas of bronchial epithelium closest to the carcinomas frequently show the most molecular abnormalities (3p, 17p, 9p, 5q). In particular, the short arm of chromosome 3 has been shown to frequently harbor deletions of alleles in several regions including 3p25-26, 3p21.3-22, 3p14 and 3p12. These regions are presumed to be the site of tumor suppressor genes, and loss of chromosome 3p allelles have shown to be an early event in lung tumorigenesis.

Chromosomal alterations in several cancers have been investigated, and frequent LOH at chromosome 10 has been reported in a variety of cancers, including glioma, glioblastoma multiforme, prostate cancer, endometrial cancer, chondrosarcome, bladder cancer, malignant melanoma, and follicular thyroid tumors ((Licciardello et al., 1989; Auerbach et al., *N. Engl J. Med.,* 265: 253-267, 1961; Voravud, et al., 1993; Feder et al., 1998; Yanagisawa et al., 1996; Thiberville et al., 1995; Papadimitrakopoulou et al., 1996; Zou et al., 1998; Brugal et al., 1984; Dalquen et al., 1997; Muguerza et al., 1997).

Deletion rates of chromosome 3p are known to correlate with lung cancer. However, there is no current clinical method for the identifying a population of individuals who are at a high risk to develop lung cancers or upper airway primary or secondary cancers. A technique for determining the risks of developing these cancers would be of great value for the ability to limit exposure to additional environmental risk factors and to know when additional tests, supplements, or treatments are appropriate.

In various studies, chromosome deletions have been studied as identifiers for lung cancers. For example, Shiseki et al., (1996) analyzed 85 loci on all 22 autosomal chromosomes to determine that the incidence of LOH on chromosome arms 2q, 9p, 18q, and 22 q in brain metastases were significantly higher than that in stages I primary lung tumors. Mitsudomi et al. (1996) used PCR-based analysis for the detection of LOH in non-small cell lung cancer. Multiple regions on chromosome 3p were observed to show that deletions of the 3p chromosome may help to identify non-small cell lung cancer patients with a poor prognosis. Wistuba et al. (2000) used fifty-four polymorphic markers used to study the entire chromosome arm 3p and concluded that 3p allele loss is nearly universal in lung cancer pathogenesis. Wu et al. (1998) studied 3p21.3 deletion using the probe, D3S4604/luca. Peripheral blood lymphocytes of 40 lung cancer patients were observed to give the conclusion that lung cancer patients exposed to benzo[α]pyrene, a common byproduct of tobacco smoke, have frequent deletions in peripheral blood lymphocytes. Shriver et al. (1998) studied lung cancer cell lines and identified the human homolog of the L14 ribosomal protein gene, RPL14; deletion of RPL14 was shown to be related to the development of lung cancer. None of theses studies, however, are able to predict the susceptibility of a patient to the development of lung cancer or to predict whether smokers and non smokers are at a high risk of developing lung or other smoking related cancers.

Because of the grim prognosis of lung cancer with a ten year survival rate of <5% the only curable cancers are those diagnosed in the early stages and treated surgically. There is a shift of interest towards diagnosis and study of early and preneoplastic states. Because early detection and effective chemoprevention therapy have potential to be curative, it is imperative to stratify the patients in clinical trials. These patients need to be monitored fore results of chemoprevention therapy and also for predictions whether a particular preneoplastic lesion may progress.

SUMMARY OF THE INVENTION

The present invention provides probes located on chromosomes 3p21.3 and 10q22 useful in the diagnosis and prognosis of cancers related to smoking. In one embodiment, a method for identifying a subject at high risk for the development, recurrence, or metastasis of cancer comprising the steps of (a) obtaining a test sample from a subject; (b) providing a nucleic acid probe targeting RPL14, CD39L3, PMGM, or GC20; (c) contacting the probe with the test sample; and (d) analyzing DNA from the sample whereby aberrations in the hybridization of said probe to said DNA was compared to wild type DNA, indicating the risk for the development, recurrence, or metastasis of cancers.

More specifically the method identifies the risk for the development of cancers. The cancer may be lung, upper airway primary or secondary, head or neck, bladder, kidneys, pancreas, mouth, throat, pharynx, larynx, esophagus, brain, liver, spleen, kidney, lymph node, small intestine, pancreas, blood cells, colon, stomach, breast, endometrium, prostate, testicle, ovary, skin, bone marrow and blood cancer. In preferred embodiments, the cancer is lung cancer. The test sample can include, but is not limited to, a surgical or biopsy specimen, paraffin embedded tissue, frozen tissue, surgical fine needle aspirations, bronchial brushes, bronchial washes, bronchial lavages, buccal smears, sputa, peripheral blood lymphocytes, esophageal brush, a fine needle aspiration, urinary specimens such as bladder washings and voided urine, and esophageal washes.

In one embodiment, it is provided that the subject can come from a group comprising smokers, former smokers, or non-smokers. In a similar embodiment, the test sample comes from said subject who has not previously been diagnosed with cancer.

It is a further embodiment of this invention that additional testing, agents or treatments may be performed after the risk for the development of said cancers has been analyzed. This includes, but is not limited to, a spiral CT-scan, cancer therapies and pharmaceutical treatments which can include radiotherapeutic agents, surgical treatment for removal of the cancerous growth, chemotherapeutic agents, antibiotics, alkylating agents and antioxidants, biological modifying respidase drugs and other agents. These agents and treatments can be used alone or in combination with other agents.

In certain embodiments, it is contemplated that FISH is used to measure the aberrations in the particular loci. A unique 3p21.3 probe can be from 1000 to 2000 base pairs or larger and used for detection in a region of about 180,000 base pairs. The probe can be labeled with a fluorophore, or more specifically digoxigenin. A specific 10q22 probe can be used in conjunction with the 3p21 probe. In certain embodiments, a control probe is used which can be labeled with a fluorophore, or more specifically spectrum orange. The control probe is a chromosome 3 stable marker or more specifically Centromere 3 (CEP 3).

In another embodiment, there is provided a method for identifying a subject at high risk for the development, recurrence, or metastasis of cancer comprising: (a) obtaining a lung test sample from a subject; (b) providing a specific 10q22 DNA probe; (c) contacting said probe with said test sample; and (d) analyzing DNA from said test sample, whereby aberrations in the hybridization of said probe to said DNA is compared to wild type DNA, indicating the risk for the development, recurrence or metastasis of said cancers. More specifically the method identifies the risk of the recurrence or metastasis of cancers. In a further embodiment, the probe size is from 1000 to 2000 base pairs or larger, for detection in a region of about 200,000 base pairs. In an additional embodiment, a specific 3p21 probe can be used with the 10q22 DNA probe. The control probe is a chromosome 10 stable marker, or more specifically Centromere10 (CEP10).

In another embodiment, there is provided a method for predicting the progression or metastasis of non-small cell carcinoma and other carcinoma in a subject comprising: (a) obtaining a test sample from a subject; (b) providing a RPL14, CD39L3, PMGM, or GC20 gene probe; (c) contacting said probe with said test sample; and (d) analyzing DNA from said test sample.

In yet another embodiment, there is provided a method for predicting the progression or metastasis of non-small cell carcinoma in a subject comprising: (a) obtaining a lung test sample from a subject; (b) providing a specific10q22 DNA probe; (c) contacting said probe with said test sample; and (d) analyzing DNA from said test sample.

In a further embodiment, there is provided a method for the staging lung of cancer in a subject comprising determining the deletion distribution of the 3p21.3 region.

In one embodiment, there is provided a method of determining likelihood of relapse or a new primary for a cancer subject comprising determining genetic aberrations at chromosomal loci 3p21.3 or 10q22 in DNA of bronchial tissue adjacent to tumor tissue from said subject, wherein abnormalities in DNA of said adjacent tissue correlate with relapse of said cancer. The cancer can comprise lung cancer or more specifically non-small cell carcinoma, adenocarcinoma, or squamous cell carcinoma. A specific gene probe may comprise RPL 14, CD39L3, PMGM, or GC20, or a 10q22 DNA probe. The 10q22 probe lies adjacent to the PTEN gene which is frequently involved non-small cell cancer. Both the 3p and the 10q probe can be used simultaneously. The test sample can be chosen from the same or contralateral lung, and can consist of tumorous or nontumorous bronchial cells.

In yet another embodiment, there is provided a method of identifying an individual to be segregated from a high risk environment comprising: (a) obtaining a test sample from a subject; (b) providing a gene probe containing RPL14, CD39L3, PMGM, and GC20 genes and PTEN or a 10q22 DNA probe, (c) contacting said probe with said test sample; and (d) analyzing DNA from said test sample, whereby said analysis is used to identify an individual who is highly susceptible to the development of lung cancer and who should not be exposed to a high risk environment.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIG. 1—3p Relapse Status. 3p21 and 10q22 deletion rates in adjacent bronchial epithelial cells of patients with benign lung disease, patients who developed stage 1 non-small cell cancer that did not relapse, and patients with stage 1 non-small cell cancer with relapse compared to 95% C1 N3P. Open squares indicate that the subjects are smokers, closed circles indicate that the subjects do not smoke (p<0.001).

FIG. 2—10q Relapse Status. 10q22 deletion rates in adjacent bronchial epithelial cells of patients with benign lung disease, patients who developed stage 1 non-small cell cancer that did not relapse, and patients with stage 1 non-small cell cancer with relapse compared to 95% C1 N10Q. Open squares indicate that the subjects are smokers, closed circles indicate that the subjects do not smoke (p<0.001).

FIG. 3—Lung Cancer Tissues. Diagram of tissue demonstrating histogenesis of lung cancer.

FIG. 4.—Percentage of Tumor cells in Dilutions. Chart showing the percentage of cells with 3p21.33 deletion detected by FISH relative to the concentration of a dilution sample.

FIG. 5—Normal Metaphase Cells. Microscope images where normal cells typically display 2 CEP3 (orange) signals and 2 3p21.33 (green) signals and tumor cells display 3 CEP3 (orange) signals and 2 3p21.33 (green) signals.

FIG. 6—Normal Interphase Cells (Lymphocytes). Microscope images where normal cells typically display 2 CEP3 (orange) signals and 2 3p21.33 (green) signals and tumor cells display 3 CEP3 (orange) signals and 2 3p21.33 (green) signals.

FIG. 7—Normal Bronchial Wash Cell. Microscope images where normal cells typically display 2 CEP3 (orange) signals and 2 3p21.33 (green) signals and tumor cells display 3 CEP3 (orange) signals and 2 3p21.33 (green) signals.

FIG. 8—Lung Cancer Cells. Microscope images where normal cells typically display 2 CEP3 (orange) signals and 2 3p21.33 (green) signals and tumor cells display 3 CEP3 (orange) signals and 2 3p21.33 (green) signals.

FIG. 9—Lung Cancer Cells. Microscope images where normal cells typically display 2 CEP3 (orange) signals and 2 3p21.33 (green) signals and tumor cells display 3 CEP3 (orange) signals and 2 3p21.33 (green) signals.

FIG. 10—10Q as a Predictor of Relapse. In a multivariate analysis, looking at the outcome in 96 patients, the deletion of 10Q in adjacent bronchial epithelial cells is a significant predictor of relapse.

FIG. 11—10Q as a Predictor of Long Term Survival. In a multivariate analysis, looking at the outcome in 96 patients, the deletion of 10Q in adjacent bronchial epithelial cells is a significant predictor of relapse long term survival.

DETAILED DESCRIPTION OF THE PREFERRED EMBODIMENTS

I. The Present Invention

Figure 1:
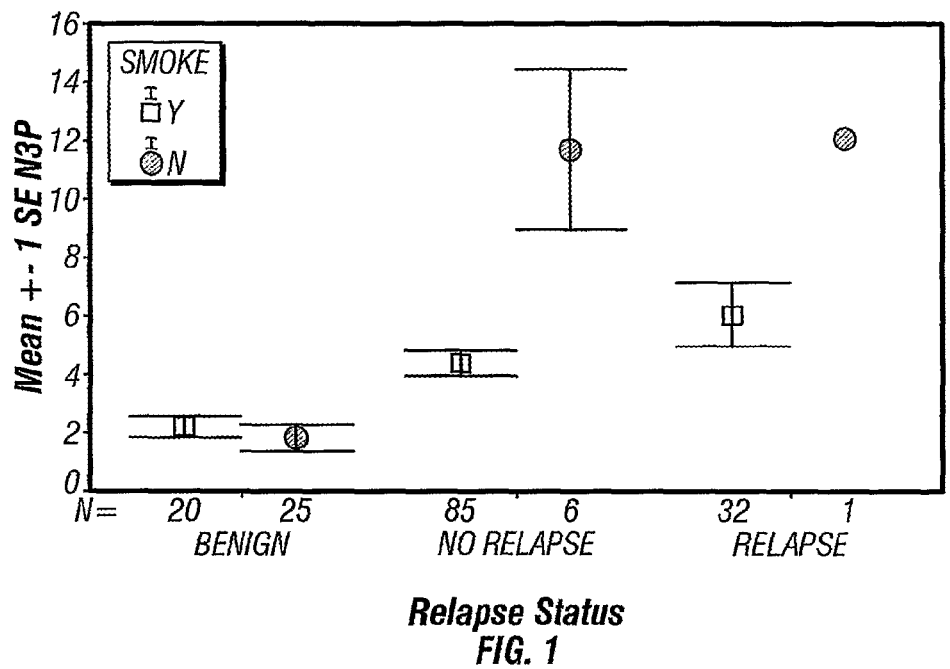

As stated above, deletions in the 3p21.3 and 10q22 regions of human chromosomes 3 and the 10 have been shown to be associated with cancers. The present invention has shown these regions also to be predictive of the development of neoplasia and progression of neoplastic events. In particular embodiments, the inventors have developed novel DNA FISH probes and tested them on patients at M. D. Anderson Cancer Center (MDACC) in early stage non-small cell lung neoplasms using archival tissue from stage I non-small cell cancers.

The probes are used in the early detection of cancer and in chemopreventive studies as an intermediate biomarker. Until now there have been no reports about the application of these DNA probes to paraffin embedded clinical tumor specimens using fluorescence in situ hybridization (FISH) and microdissection. The FISH technique allows the measurement of an average level of deletion of a gene in a tumor, as well as the actual number and distribution of the gene in individual, morphological cells. The inventors propose that deletion distribution of the RPL14, CD39L3, PMGM or GC20 genes and 10q22 locus are useful as a diagnostic tool in determining the stage of lung cancer patients.

A. Smoking Related Cancers

The current invention is useful for the prognosis and diagnosis of lung cancers, which can be defined by a number of histologic classifications including: squamous cell carcinomas such as squamous carcinoma; small cell carcinomas such as oat cell carcinoma, intermediate cell type carcinoma, combined oat and cell carcinoma; adenocarcinomas such as acinar adenocarcinoma, papillary adenocarcinoma, bronchioloalveolar carcinoma, and solid carcinoma with mucus formation; large cell carcinoma such as giant cell carcinoma and clear cell carcinoma; adenosquamous carcinoma; carcinoid; and bronchial gland carcinomas such as adenoid cystic, and mucoepidermoid carcinoma. Diagnosis and prognosis of other smoking related cancers is possible with these probes. Squamous cell carcinoma of the head and neck has the same risk factors as lung cancer is hypothesized to have similar etiology (Shriver, 1998). Similarly, smoking is an etiological factor for cancer of the bladder, head, neck, kidneys, pancreas, and cancer of the upper airways including cancer of the mouth, throat, pharynx, larynx, or esophagus.

B. Tumorgenesis

The deletions of various genes in tumor tissue has been well studied in the art. However, there remains a need for probes that are significant for detecting early molecular events in the development of cancers, as well as molecular events that make patients susceptible to the development of cancer. Probes used for the staging of cancer are also of interest. The proposed sequence leading to tumorigenesis includes genetic instability at the cellular or submicroscopic level as demonstrated by loss or gain of chromosomes, leading to a hyperproliferative state due to theoretical acquisition of factors that confer a selective proliferative advantage. Further, at the genetic level, loss of function of cell cycle inhibitors and tumor suppressor genes (TSG), or amplification of oncogenes that drive cell proliferation, are implicated.

Following hyperplasia, a sequence of progressive degrees of dysplasia, carcinoma-in-situ and ultimately tumor invasion is recognized on histology. These histologic changes are both preceded and paralleled by a progressive accumulation of genetic damage. At the chromosomal level genetic instability is manifested by a loss or gain of chromosomes, as well as structural chromosomal changes such as translocation and inversions of chromosomes with evolution of marker chromosomes. In addition cells may undergo polyploidization. Single or multiple clones of neoplastic cells may evolve characterized in many cases by aneuploid cell populations. These can be quantitated by measuring the DNA content or ploidy relative to normal cells of the patient by techniques such as flow cytometry or image analysis.

C. Prognostic Factors and Staging

At present, the most important prognostic factor regarding the survival of patients with lung cancer of non-small cell type is the stage of disease at diagnosis. Small cell cancer usually presents with wide spread dissemination hence the staging system is less applicable. The staging system was devised based on the anatomic extent of cancer and is now know as the TNM system based on anatomical size and spread within the lung and adjacent structures, regional lymph nodes and distant metastases. The only hope presently for a curative procedure lies n the operability of the tumor which can only be resected when the disease is at a low sage, that is confined to the lung.

| Occult Carcinoma | |
|---|---|
| TX NO MO | Occult carcinoma with bronchopulmonary secretions containing malignant cells but without other evidence of the primary tumor or evidence of metastasis |
| Stage 1 | |
| TIS NO MO | Carcinoma in situ |
| T1 NO MO | Tumor that can be classified T1 without any metastasis to the regional lymph nodes |
| T1 N1 MO | Tumor that can be classified T1 with metastasis to the lymph nodes in the ipsilateral hilar region only |
| T2 N1 MO | Tumor that can be classified T2 without any metastasis to nodes or distant metastasis |
| Stage II | |
| T2 N1 MO | Tumor classified as T2 with metastasis to the lymph nodes in the ipsilateral hilar region only |
| Stage III | |
| T3 with an N or M | Any tumor more extensive than T2 |
| N2 with an T or M | Any tumor with metastasis to the lymph nodes in the mediastinum |
| M1 with any T or N | Any tumor with distant metastasis |

D. Grading of Tumors

The histological type and grade of lung cancer do have some prognostic impact within the stage of disease with the best prognosis being reported for stage I adenocarcinoma, with 5 year survival at 50% and 1-year survival at 65% and 59% for the bronchiolar-alveolar and papillary subtypes (Naruke et al., 1988; Travis et al., 1995; Carriaga et al., 1995). For squamous cell carcinoma and large cell carcinoma the 5 year survival is around 35%. Small cell cancer has the worst prognosis with a 5 year survival rate of only 12% for patients with localized disease (Carcy et al., 1980; Hirsh, 1983; Vallmer et al., 1985). For patients with distant metastases survival at 5 years is only 1-2% regardless of histological subtype (Naruke et al., 1988). In addition to histological subtype, it has been shown that histological grading of carcinomas within subtype is of prognostic value with well differentiated tumors having a longer overall survival than poorly differentiated neoplasms. Well differentiated localized adencarcinoma has a 69% overall survival compared to a survival rate of only 34% of patients with poorly differentiated adenocarcinoma (Hirsh, 1983). The 5 year survival rates of patients with localized squamous carcinoma have varied from 37% for well differentiated neoplasms to 25% for poorly differentiated squamous carcinomas (Ihde, 1991).

The histologic criteria for subtyping lung tumors is as follows: squamous cell carcinoma consists of a tumor with keratin formation, keratin pearl formation, and/or intercellular bridges. Adenocarcinomas consist of a tumor with definitive gland formation or mucin production in a solid tumor. Small cell carcinoma consists of a tumor composed of small cells with oval or fusiform nuclei, stippled chromatin, and indistinct nuclei. Large cell undifferentiated carcinoma consists of a tumor composed of large cells with vesicular nuclei and prominent nucleoli with no evidence of squamous or glandular differentiation. Poorly differentiated carcinoma includes tumors containing areas of both squamous and glandular differentiation.

E. Development of Carcinomas

The evolution of carcinoma of the lung is most likely representative of a field cancerization effect as a result of the entire aero-digestive system being subjected to a prolonged period of carcinogenic insults such as benzylpyrenes, asbestosis, air pollution and chemicals other carcinogenic substances in cigarette smoke or other environmental carcinogens. This concept was first proposed by Slaughter et al. (1953). Evidence for existence of a field effect is the common occurrence of multiple synchronous for metachronous second primary tumors (SPTs) that may develop throughout the aero-digestive tract in the oropharynx, upper esophagus or ipsilateral or contralateral lung.

Accompanying these molecular defects is the frequent manifestation of histologically abnormal epithelial changes including hyperplasia, metaplasia, dysplasia, and carcinoma-in-situ. It has been demonstrated in smokers that both the adjacent normal bronchial epithelium as well as the preneoplastic histological lesions may contain clones of genetically altered cells. (Wistuba et al., 2000).

Liciardello et al. (1989) found a 10-40% incidence of metachronous tumors and a 9-14% incidence of synchronous SPTs in the upper and lower aero-digestive tract, mostly in patients with the earliest primary tumors SPTs may impose a higher risk than relapse from the original primary tumor and may prove to be the major threat to long term survival following successful therapy for early stage primary head, neck or lung tumors. Hence it is vitally important to follow these patients carefully for evidence of new SPTs in at risk sites for new malignancies specifically in the aero-digestive system.

In addition to chromosomal changes at the microscopic level, multiple blind bronchial biopsies may demonstrate various degrees of intraepithelial neoplasia at loci adjacent to the areas of lung cancer. Other investigators have shown that there are epithelial changes ranging from loss of cilia and basal cell hyperplasia to CIS in most light and heavy smokers and all lungs that have been surgically resected for cancer. (Auerbach et al., 1961). Voravud et al. (1993) demonstrated by in-situ hybridization (ISH) studies using chromosome-specific probes for chromosomes 7 and 17 that 30-40% of histologically normal epithelium adjacent to tumor showed polysomies for these chromosomes. In addition there was a progressive increase in frequency of polysomies in the tissue closest to the carcinoma as compared to normal control oral epithelium from patients without evidence of carcinoma. The findings of genotypic abnormalities that increased closer to the area of the tumor support the concept of field cancerization. Interestingly there was no increase in DNA content as measured in the normal appearing mucosa in a Feulgen stained section adjacent to the one where the chromosomes were measured, reflecting perhaps that insufficient DNA had been gained in order to alter the DNA index. Interestingly a very similar increase in DNA content was noted both in dysplastic areas close to the cancer and in the cancerous areas suggesting that complex karyotypic abnormalities that are clonal have already been established in dysplastic epithelium adjacent to lung cancer. Others have also shown an increase in number of cells showing p53 mutations in dysplastic lesions closest to areas of cancer, which are invariably also p53 mutated. Other chromosomal abnormalities that have recently been demonstrated in tumors and dysplastic epithelium of smokers includes deletions of 3p, 17p, 9 p and 5q (Feder et al., 1998; Yanagisawa et al., 1996; Thiberville et al., 1995).

F. Chromosome Deletions in Lung Cancer

Small cell lung cancer (SCLC) and non-small cell lung cancer commonly display cytogenetically visible deletions on the short arm of chromosome 3 (Hirano et al., 1994; Valdivieso et al., 1994; Cheon et al., 1993; Pence et al., 1993). This 3p deletion occurs more frequently in the lung tumor tissues of patients who smoke than it does in those of non-smoking patient. (Rice et al., 1993) Since approximately 85% lung cancer patients were heavy cigarette smokers (Mrkve et al., 1993), 3p might contain specific DNA loci related to the exposure of tobacco carcinogens. It also has been reported that 3p deletion occurs in the early stages of lung carcinogenesis, such as bronchial dysplasia (Pantel et al., 1993). In addition to cytogenetic visible deletions, loss of heterozygosity (LOH) studies have defined 3-21.3 as one of the distinct regions that undergo loss either singly or in combination (Fontanini et al., 1992; Liewald et al., 1992). Several other groups have found large homozygous deletions at 3p21.3 in lung cancer (Macchiarini et al., 1992; Miyamoto et al., 1991; Ichinose et al., 1991; Yamaoka et al., 1990). Transfer of DNA fragments from 3-21.3-3p21.2 into lung tumor cell lines could suppress the tumorigenesis. (Sahin et al., 1990; Volm et al., 1989). These finding strongly suggest the presence of at least one tumor suppressor gene in this specific chromosome region whose loss will initiate lung carcinogenesis.

Cytogenetic observation of lung cancer has shown an unusual consistency in the deletion rate of chromosome 3p. In fact, small cell lung cancer (SCLC) demonstrates a 100% deletion rate within certain regions of chromosome 3p. Non small cell lung cancer (NSCLC) demonstrates a 70% deletion rate (Mitsudomi et al., 1996; Shiseki et al., 1996). Loss of heterozygosity and comparative genomic hybridization analysis have shown deletions between 3p14.2 and 3p21.3 to be the most common finding for lung carcinoma and is postulated to be the most crucial change in lung tumorigenesis (Wu et al., 1998). It has been hypothesized that band 3p21.3 is the location for lung cancer tumor suppressor genes. The hypothesis is supported by chromosome 3 transfer studies, which reduced tumorigenicity in lung adenocarcinoma.

Allelotype studies on non-small cell lung carcinoma indicated loss of genetic material on chromosome 10q in 27% of cases. Studies of chromosome 10 allelic loss have shown that there is a very high incidence of LOH in small cell lung cancer, up to 91%. (Alberola et al., 1995; Ayabe et al., 1994). A statistically significant LOH of alleles on 10q was noted in metastatic squamous cell carcinoma (SCC) in 56% of cases compared to non-metastatic SCC with LOH seen in only 14% of cases. (Ayabe et al., 1994). No LOH was seen in other subtypes on NSCLC. Peterson (1995) used paired samples of tumor and normal tissue to assess LOB. By micro-satellite polymorphism analysis, a high incidence of loss was found between D10s677 and D10S1223. This region spans the long arm of chromosome 10 at bands q21-q24 and overlaps the region deleted in the a study of advanced stage high grade bladder cancers which demonstrated a high frequency of allele loss within a 2.5cM region at 10q22.3-10q23.1 (Kim et al., 1996).

II. The 3p21.3 Gene Probes

A. Structural Features

Recently, the human ribosomal L14 (RPL14) gene (GenBank Accession NM_003973, SEQ ID NO: 1), and the genes CD39L3 (GenBank Accession AAC39884 and AF039917; SEQ ID NO: 3), PMGM (GenBank Accession P15259 and J05073; SEQ ID NO: 5), and GC20 (GenBank Accession NM_005875; SEQ ID NO: 7) were isolated from a BAC (GenBank Accession AC019204, herein incorporated by reference) and located in the 3p21.3 band within the smallest region of deletion overlap of various lung tumors. The RPL14 gene sequence contains a highly polymorphic trinucleotide (CTG) repeat array, which encodes a variable length polyalanine tract. Polyalanine tracts are found in gene products of developmental significance that bind DNA or regulate transcription. For example, *Drosophila* proteins Engrailed, Krup- pel and Even-Skipped all contain polyalanine tracts that act as transcriptional repressors. Genotype analysis of RPL14 shows that this locus is 68% heterozygous in the normal population, compared with 25% in NSCLC cell lines. Cell cultures derived from normal bronchial epithelium show a 65% level of heterozygosity, reflecting that of the normal population.

B. Functional Aspects

Genes with a regulatory function such as the RPL14 gene (SEQ ID NO: 1), along with the genes CD39L3, PMGM, and GC20 (SEQ ID NOS: 3, 5 and 7) and analogs thereof, are good candidates for diagnosis of tumorigenic events. It has been postulated that functional changes of the RPL14 protein (SEQ ID NO: 2) can occur via a DNA deletion mechanism of the trinucleotide repeat encoding for the protein. This deletion mechanism makes the RPL14 gene and attractive sequence that may be used as a marker for the study of lung cancer risk (Shriver et al., 1998). In addition, the RPL14 gene shows significant differences in allele frequency distribution in ethnically defined populations, making this sequence a useful marker for the study of ethnicity adjusting lung cancer (Shriver et al., 1998). Therefore, this gene is useful in the early detection of lung cancer, and in chemopreventive studies as an intermediate biomarker.

III. The 10q22 Gene Probes

A. Structural Features

The 10q22 BAC (46b12) is 200 Kb and is adjacent and centromeric to PTEN/MMAC1 (GenBank Accession AF067844), which is at 10q22-23 and can be purchased through Research Genetics (Huntsville, Ala.). Alterations to 10q22-25 has been associated with multiple tumors, including lung, prostate, renal, and endometrial carcinomas, melanoma, and meningiomas, suggesting the possible suppressive locus affecting several cancers in this region. The PTEN/MMAC1 gene, encoding a dual-specificity phosphatase, is located in this region, and has been isolated as a tumor suppressor gene that is altered in several types of human tumors including brain, bladder, breast and prostate cancers. PTEN/MMAC1 mutations have been found in some cancer cell lines, xenografts, and hormone refractory cancer tissue specimens. Because the inventor's 10q22 BAC DNA sequence is adjacent to this region, the DNA sequences in the BAC 10q22 may be involved in the genesis and/or progression of human lung cancer.

B. Functional Aspects

Functional evidence for the presence of tumor suppressor genes on 10q has been provided by microcell-mediated chromosomal transfer. The resulting hybrid clones displayed a suppressed tumorigenic phenotype with the inability to proliferate in nude mice and soft agarose. Sequence analysis of the PTEN/MMAC1 gene in lung cancer revealed a G to C substitution located 8 bp upstream of the coding region of exon1 and which seems to be a polymorphism, in 4 of the 30 cases of lung cancer tested. Somatic mutations of the TPEN/MMAC1 gene were not identified in any of the tumors at the primary and metastatic sites of lung cancer, indicating that point mutations in the PTEN/MMAC1 gene are probably not an important factor in tumorigenesis and the progression of a major subset of lung cancers. Other more important tumor suppressor genes must lie close to the PTEN/MMAC1 gene, in the vicinity of the inventors' 10q22 BAC locus. Therefor, the 10q22 probe is useful in the further development of clinical biomarkers for the early detection of neoplastic events, for risk assessment and monitoring the efficacy of chemoprevention therapy in high risk former or current smokers.

IV. Nucleic Acids

The inventors' have identified the probes for the human chromosome region 3p21.3 and human chromosome region 10q22. In addition, it should be clear that the present invention is not limited to the specific nucleic acids disclosed herein.

A. Probes and Primers

Naturally, the present invention encompasses DNA segments that are complementary, or essentially complementary, to target sequences. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to a target nucleic acid segment under relatively stringent conditions such as those described herein. These probes may span hundreds or thousands of base pairs.

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of about 8, 9, 10, 11, 12, 13, 14, 15, 16, 17, 18, 19, 20, 25, 30, 35, 40, 45, 50, 55, 60, 65, 70, 75, 80, 85, 90, 95, 100, 250, 500, 700, 722, 900, 992, 1000, 1500, 2000, 2500, 2800, 3000, 3500, 3800, 4000, 5000 or more base pairs will be used, although others are contemplated. As mentioned above, longer polynucleotides encoding 7000, 10000. 12000 bases and longer are contemplated as well. Such oligonucleotides will find use, for example, as probes in FISH, Southern and Northern blots and as primers in amplification reactions.

It will be understood that this invention is not limited to the particular probes disclosed herein and particularly is intended to encompass at least nucleic acid sequences that are hybridizable to the disclosed sequences or are functional sequence analogs of these sequences. For example, a partial sequence may be used to identify a structurally-related gene or the full length genomic or cDNA clone from which it is derived. Those of skill in the art are well aware of the methods for generating cDNA and genomic libraries which can be used as a target for the above-described probes (Sambrook et al., 1989).

For applications in which the nucleic acid segments of the present invention are incorporated into vectors, such as plasmids, cosmids or viruses, these segments may be combined with other DNA sequences, such as promoters, polyadenylation signals, restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol.

DNA segments encoding a specific gene may be introduced into recombinant host cells and employed for expressing a specific structural or regulatory protein. Alternatively, through the application of genetic engineering techniques, subportions or derivatives of selected genes may be employed. Upstream regions containing regulatory regions such as promoter regions may be isolated and subsequently employed for expression of the selected gene.

B. Labeling of Probes

In certain embodiments, it will be advantageous to employ nucleic acid sequences of the present invention in combination with an appropriate means, such as a label, for determining hybridization. A wide variety of appropriate indicator means are known in the art, including fluorescent, radioactive, chemiluminescent, electroluminescent, enzymatic tag or other ligands, such as avidin/biotin, antibodies, affinity labels, etc., which are capable of being detected. In preferred embodiments, one may desire to employ a fluorescent label such as digoxigenin, spectrum orange, fluorosein, eosin, an acridine dye, a rhodamine, Alexa 350, Alexa 430, AMCA, BODIPY 630/650, BODIPY 650/665, BODIPY-FL, BODIPY-R6G, BODIPY-TMR, BODIPY-TRX, cascade blue, Cy2, Cy3, Cy5,6-FAM, HEX, 6-JOE, Oregon green 488, Oregon green 500, Oregon green 514, pacific blue, REG, ROX, TAMRA, TET, or Texas red.

In the case of enzyme tags such as urease alkaline phosphatase or peroxidase, colorimetric indicator substrates are known which can be employed to provide a detection means visible to the human eye or spectrophotometrically, to identify specific hybridization with complementary nucleic acid-containing samples. Examples of affinity labels include but are not limited to the following: an antibody, an antibody fragment, a receptor protein, a hormone, biotin, DNP, or any polypeptide/protein molecule that binds to an affinity label and may be used for separation of the amplified gene.

The indicator means may be attached directly to the probe, or it may be attached through antigen bonding. In preferred embodiments, digoxigenin is attached to the probe before denaturization and a fluorophore labeled anti-digoxigenin FAB fragment is added after hybridization.

C. Hybridization Conditions

Suitable hybridization conditions will be well known to those of skill in the art. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 μM $MgCl_2$, at temperatures ranging from approximately 40° C. to about 72° C. Formamide and SDS also may be used to alter the hybridization conditions.

V. Biomarkers

Various biomarkers of prognostic significance can be used in conjunction with the 3p21.3 or the 10q22 nucleic acid probes. These biomarkers could aid in predicting the survival in low stage cancers and the progression from preneoplastic lesions to invasive lung cancer. These markers can include proliferation activity as measured by Ki-67 (MIB1), angiogenesis as quantitated by expression of VEGF and microvessels using CD34, oncogene expression as measured by erb B2, and loss of tumor suppresser genes as measured by p53 expression.

Multiple biomarker candidates have been implicated in the evolution of neoplastic lung lesions. Bio-markers that have been studies include general genomic markers including chromosomal alterations, specific genomic markers such as alterations in proto-oncogenes such as K-Ras, Erbβ1/EGFR, Cyclin D; proliferation markers such as Ki67 or PCNA, squamous differentiation markers, and nuclear retinoid receptors (Papadimitrakopoulou et al., 1996) The latter are particularly interesting as they may be modulated by specific chemopreventive drugs such as 13-cis-retinoic acid or 4HPR and culminate in apoptosis of the defective cells with restoration of a normally differentiated mucosa (Zou et al., 1998).

A. Tumor Angiogenesis by Microvessel Counts

Tumor angiogenesis can be quantitated by microvessel density and is a viable prognostic factor in stage 1 NSCLC. Tumor microvessel density appears to be a good predictor of survival in stage 1 NSCLC.

B. Vascular Endothelial Growth Factor (VEGF)

VEGF (3, 6-8 ch 4) an endothelial cell specific mitogen is an important regulator of tumor angiogenesis who's expression correlates well with lymph node metastases and is a good indirect indicator of tumor agniogenesis. VEGF in turn is upregulated by P53 protein accumulation in NSCLC.

C. p53

The role of p53 mutations in predicting progression and survival of patients with NSCLC is widely debated. Although few studies imply a negligible role, the majority of the studies provide compelling evidence regarding the role of p53 as one of the prognostic factors in NSCLC. The important role of p53 in the biology of NSCLC has been the basis for adenovirus mediated p53 gene transfer in patients with advanced NSCLC (Carcy et al., 1980). In addition p53 has also been shown to be an independent predictor of chemotherapy response in NSCLC. In a recent study (Valimer et al., 1985), the importance of p53 accumulation in preinvasive bronchial lesions from patients with lung cancer and those who did not progress to cancer were studied. It was demonstrated that p53 accumulation in preneoplastic lesions had a higher rate of progression to invasion than did p53 negative lesions.

D. c-erb-B2

Similar to p53, c-erg-B2 (Her2/neu) expression has also been shown to be a good marker of metastatic propensity and an indicator of survival in these tumors.

E. Ki-67 Proliferation Marker

In addition to the above markers, tumor proliferation index as measured by the extent of labeling of tumor cells for Ki-67, a nuclear antigen expressed throughout cell cycle correlates significantly with clinical outcome in Stage 1 NSCLC (Feinstein et al., 1970). The higher the tumor proliferation index the poorer is the disease free survival labeling indices provides significant complementary, if not independent prognostic information in Stage 1 NSCLC, and helps in the identification of a subset of patients with Stage 1 NSCLC who may need more aggressive therapy.

VI. Prognosis and Diagnosis of Cancers Using 3p21.3 and 10q22 Gene Probes

Alterations in the 3p21.3 and 10q22 loci are known to be associated with a number of cancers. More specifically, point mutations, deletions, insertions or regulatory perturbations relating to the 3p21.3 and 10q22 loci may cause cancer or promote cancer development, cause or promoter tumor progression at a primary site, and/or cause or promote metastasis. Other phenomena at the 3p21.3 and 10q22 loci include angiogenesis and tissue invasion. Thus, the present inventors have demonstrated that deletions at 3p21.3 and 10q22 can be used not only as a diagnostic or prognostic indicator of cancer, but to predict specific events in cancer development, progression and therapy.

A variety of different assays are contemplated in this regard, including but not limited to, fluorescent in situ hybridization (FISH), direct DNA sequencing, PFGE analysis, Southern or Northern blotting, single-stranded conformation analysis (SSCA), RNase protection assay, allele-specific oligonucleotide (ASO), dot blot analysis, denaturing gradient gel electrophoresis, RFLP and PCR-SSCP.

Various types of defects are to be identified. Thus, "alterations" should be read as including deletions, insertions, point mutations and duplications. Point mutations result in stop codons, frameshift mutations or amino acid substitutions. Somatic mutations are those occurring in non-germline tissues. Germ-line tissue can occur in any tissue and are inherited.

A. Samples

One embodiment of the instant invention comprises a method for detecting variation in the hybridization of the probes to DNA. This may comprise determining specific alterations in the expressed product, or may simply involve detecting gross structural abnormalities. Such cancer may involve cancers of the lung, upper airway primary or secondary cancer, bladder, urithial, head and neck, esophagus, kidney, pancreas, mouth, throat, pharynx, larynx, brain, liver, spleen, small intestine, blood cells, lymph node, colon, breast, endometrium, stomach, prostate, testicle, ovary, skin, bone marrow, blood or other tissue.

In particular, the present invention relates to the diagnosis and prognosis of smoking related cancers. More particularly, the present invention relates to the diagnosis and prognosis of lung cancer which includes, but is not limited to: squamous cell carcinomas such as squamous carcinoma; small cell carcinomas such as oat cell carcinoma, intermediate cell type carcinoma, combined oat and cell carcinoma; adenocarcinomas such as acinar adenocarcinoma, papillary adenocarcinoma, bronchioloalveolar carcinoma, and solid carcinoma with mucus formation; large cell carcinoma such as giant cell carcinoma and clear cell carcinoma; adenosquamous carcinoma; carcinoid; and bronchial gland carcinomas such as adenoid cystic, and mucoepidermoid carcinoma.

The biological sample can be any tissue or fluid that contains nucleic acids. Various embodiments include paraffin imbedded tissue, frozen tissue, surgical fine needle aspirations, cells of the skin, muscle, lung, head and neck, esophagus, kidney, pancreas, mouth, throat, pharynx, larynx, esophagus, facia, brain, prostate, breast, endometrium, small intestine, blood cells, liver, testes, ovaries, colon, skin, stomach, spleen, lymph node, bone marrow or kidney. Other embodiments include fluid samples such as bronchial brushes, bronchial washes, bronchial lavages, peripheral blood lymphocytes, lymph fluid, ascites, serous fluid, pleural effusion, sputum, cerebrospinal fluid, lacrimal fluid, esophageal washes, stool or urinary specimens such as bladder washing and urine.

Bronchial washes sample more area of bronchial epithelium but are also frequently cytologically normal. A more complete sampling of the respiratory passages may occur with a bronchiolar alveolar lavage in which both left and right proximal and distal small bronchi and bronchioles are washed out.

Nucleic acids are isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA.

Depending on the format, the specific nucleic acid of interest is identified in the sample directly using amplification or with a second, known nucleic acid following amplification. Next, the identified product is detected. The detection may involve indirect identification of the product via fluorescent label, chemiluminescence, radioactive scintigraphy of radiolabel or even via a system using electrical or thermal impulse signals (Affymax Technology; Bellus, 1994). Alternatively, the detection may be performed by visual means (e.g., ethidium bromide staining of a gel).

Following detection, one may compare the results seen in a given sample with a statistically significant reference group of samples from normal patients and patients that have or lack alterations in chromosome loci 3p21.3 or 10q22. In this way, it is possible to correlate the amount or kind of alterations detected with various clinical states.

B. Fluorescence In Situ Hybridization

Fluorescence in situ hybridization (FISH) can be used for molecular studies. FISH is used to detect highly specific DNA probes which have been hybridized to chromosomes using fluorescence microscopy. The DNA probe is labeled with fluorescent or non fluorescent molecules which are then detected by fluorescent antibodies. The probes bind to a specific region or regions on the target chromosome. The chromosomes are then stained using a contrasting color, and the cells are viewed using a fluorescence microscope.

Each FISH probe is specific to one region of a chromosome, and is labeled with fluorescent molecules throughout it's length. Each microscope slide contains many metaphases. Each metaphase consists of the complete set of chromosomes, one small segment of which each probe will seek out and bind itself to. The metaphase spread is useful to visualize specific chromosomes and the exact region to which the probe binds. The first step is to break apart (denature) the double strands of DNA in both the probe DNA and the chromosome DNA so they can bind to each other. This is done by heating the DNA in a solution of formamide at a high temperature (70-75° C.) Next, the probe is placed on the slide and the slide is placed in a 37° C. incubator overnight for the probe to hybridize with the target chromosome. Overnight, the probe DNA seeks out it's target sequence on the specific chromosome and binds to it. The strands then slowly reanneal. The slide is washed in a salt/detergent solution to remove any of the probe that did not bind to chromosomes and differently colored fluorescent dye is added to the slide to stain all of the chromosomes so that they may then be viewed using a fluorescent light microscope. Two, or more different probes labeled with different fluorescent tags can be mixed and used at the same time. The chromosomes are then stained with a third color for contrast. This gives a metaphase or interphase cell with three or more colors which can be used to detect different chromosomes at the same time, or to provide a control probe in case one of the other target sequences are deleted and a probe cannot bind to the chromosome. This technique allows, for example, the localization of genes and also the direct morphological detection of genetic defects.

The advantage of using FISH probes over microsatellite instability to test for loss of allelic heterozygosity is that the a) FISH is easily and rapidly performed on cells of interest and can be used on paraffin-embedded, or fresh or frozen tissue allowing the use of micro-dissection b) specific gene changes can be analyzed on a cell by cell basis in relationship to centomeric probes so that true homozygosity versus heterozygosity of a DNA sequence can be evaluated (use of PCR for microsatellite instability may permit amplification of surrounding normal DNA sequences from contamination by normal cells in a homozygously deleted region imparting a false positive impression that the allele of interest is not deleted) c) PCR cannot identify amplification of genes d) FISH using bacterial artificial chromosomes (BACs) permits easy detection and localization on specific chromosomes of genes of interest which have been isolated using specific primer pairs.

C. Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in its entirety.

Briefly, in PCR, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention, Walker et al., (1992).

Strand Displacement Amplification (SDA) is another method of carrying out isothermal amplification of nucleic acids, which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPO No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, M. A., In: *PCR PROTOCOLS: A GUIDE TO METHODS AND APPLICATIONS*, Academic Press, N.Y., 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., (1989), incorporated herein by reference in its entirety.

D. Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

E. Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

F. Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols. See Sambrook et al., 1989. For example, chromophore or radiolabel probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of sequences throughout the RPL14, CD39L3, PMGM, or GC20 gene probes that may then be analyzed by direct sequencing.

G. Kit Components

All the essential materials and reagents required for detecting and sequencing RPL14, CD39L3, PMGM, or GC20 genes and variants thereof may be assembled together in a kit. This generally will comprise preselected primers and probes. Also included may be enzymes suitable for amplifying nucleic acids including various polymerases (RT, Taq, Sequenase™ etc.), deoxynucleotides and buffers to provide the necessary reaction mixture for amplification. Such kits also generally will comprise, in suitable means, distinct containers for each individual reagent and enzyme as well as for each primer or probe.

H. Chip Technologies

Specifically contemplated by the present inventors are chip-based DNA technologies such as those described by Hacia et al. (1996) and Shoemaker et al. (1996). These techniques involve quantitative methods for analyzing large numbers of genes rapidly and accurately. By tagging genes with oligonucleotides or using fixed probe arrays, one can employ chip technology to segregate target molecules as high density arrays and screen these molecules using methods such as fluorescence, conductance, mass spectrometry, radiolabeling, optical scanning, or electrophoresis. See also Pease et al. (1994); Fodor et al. (1991).

Biologically active DNA probes may be directly or indirectly immobilized onto a surface to ensure optimal contact and maximum detection. When immobilized onto a substrate, the gene probes are stabilized and therefore may be used repetitively. In general terms, hybridization is performed on an immobilized nucleic acid target or a probe molecule is attached to a solid surface such as nitrocellulose, nylon membrane or glass. Numerous other matrix materials may be used, including reinforced nitrocellulose membrane, activated quartz, activated glass, polyvinylidene difluoride (PVDF) membrane, polystyrene substrates, polyacrylamide-based substrate, other polymers such as poly(vinyl chloride), poly(methyl methacrylate), poly(dimethyl siloxane), photopolymers (which contain photoreactive species such as nitrenes, carbenes and ketyl radicals capable of forming covalent links with target molecules (Saiki, et al., 1994).

Immobilization of the gene probes may be achieved by a variety of methods involving either non-covalent or covalent interactions between the immobilized DNA comprising an anchorable moiety and an anchor. DNA is commonly bound to glass by first silanizing the glass surface, then activating with carbodimide or glutaraldehyde. Alternative procedures may use reagents such as 3-glycidoxypropyltrimethoxysilane (GOP) or aminopropyltrimethoxysilane (APTS) with DNA linked via amino linkers incorporated either at the 3' or 5' end of the molecule during DNA synthesis. Gene probe may be bound directly to membranes using ultraviolet radiation. With nitrocellous membranes, the probes are spotted onto the membranes. A UV light source is used to irradiate the spots and induce cross-linking. An alternative method for cross-linking involves baking the spotted membranes at 80° C. for two hours in vacuum.

Immobilization can consist of the non-covalent coating of a solid phase with streptavidin or avidin and the subsequent immobilization of a biotinylated polynucleotide (Holmstrom, 1993). Precoating a polystyrene or glass solid phase with poly-L-Lys or poly L-Lys, Phe, followed by the covalent attachment of either amino- or sulfhydryl-modified polynucleotides using bifunctional crosslinking reagents (Running, 1990 and Newton, 1993) can also be used to immobilize the probe onto a surface.

Immobilization may also take place by the direct covalent attachment of short, 5'-phosphorylated primers to chemically modified polystyrene plates ("Covalink" plates, Nunc) Rasmussen, (1991). The covalent bond between the modified oligonucleotide and the solid phase surface is introduced by condensation with a water-soluble carbodiimide. This method facilitates a predominantly 5'-attachment of the oligonucleotides via their 5'-phosphates.

Nikiforov et al. (U.S. Pat. No. 5,610,287) describes a method of non-covalently immobilizing nucleic acid molecules in the presence of a salt or cationic detergent on a hydrophilic polystyrene solid support containing an —OH, —C=O or —COOH hydrophilic group or on a glass solid support. The support is contacted with a solution having a pH of about 6 to about 8 containing the synthetic nucleic acid and the cationic detergent or salt. The support containing the immobilized nucleic acid may be washed with an aqueous solution containing a non-ionic detergent without removing the attached molecules.

There are two common variants of chip-based DNA technologies involving DNA microarrays with known sequence identity. For one, a probe cDNA (500~5,000 bases long) is immobilized to a solid surface such as glass using robot spotting and exposed to a set of targets either separately or in a mixture. This method, "traditionally" called DNA microarray, is widely considered as developed at Stanford University.

A recent article by Ekins and Chu (1999) provides some relevant details. The other variant includes an array of oligonucleotide (20~25-mer oligos) or peptide nucleic acid (PNA) probes is synthesized either in situ (on-chip) or by conventional synthesis followed by on-chip immobilization. The array is exposed to labeled sample DNA, hybridized, and the identity/abundance of complementary sequences are determined. This method, "historically" called DNA chips, was developed at Affymetrix, Inc., which sells its products under the GeneChip® trademark.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Lung Cancer Patients and the Correlation between RPL 14 Gene Deletion Percentage and Patient Survival Tissue Samples Normal lung tissue and cancerous lung tissue were obtained from lung biopsies embedded in paraffin blocks. These paraffin embedded histologic tissue are from a clinically and pathologically well characterized group of patients with stage 1 lung cancers that underwent resection at M. D. Anderson Cancer Center (MDACC) and were obtained from MDACC cases on file. These retrospective samples were drawn so that the retrospective samples were as fresh as possible and still have at least 2 years follow-up. Many cases had 14 years of follow up. Demographic information for these patient groups include: age at the time of diagnosis, race, gender, dietary information, initial treatment, screening test with results, date of diagnosis and follow-up with status, other diagnosis information, tobacco history, alcohol history, other diagnoses associated with tobacco or alcohol use, and other drugs or treatments which might have a chemopreventative effect.

Cell Dissociation of Interphase Nuclei from Formalin Fixed Paraffin Embedded Blocks Punch biopsies of 30 histologically representative cancerous lung tissue and adjacent normal lung tissue were performed on paraffin embedded blocks and the resulting tissue sections were placed in 1.5 ml Eppendorf tubes. The same Punch biopsy procedure was performed on 10 controls originating from normal lung tissue with no trace of cancerous growth. A dewaxing/rehydration incubation protocol, with a 3 min centrifuge (12,000 r.p.m.) between each step was performed on the tissue blocks: Xylene (30 min), Xylene (10 min), 100% Ethanol (10 min), 95% Ethanol (10 min), 70% Ethanol (10 min), 50% Ethanol (10 min), $H_2O$ (10 min), $H_2O$ (10 min).

After the incubation, scissors were inserted into the 1.5 ml Eppendorf tubes and used to finely cut the tissue. This step is critical, as it mechanically removes cells from their connective tissue surroundings. Next, 1 ml Protease K solution was added to each Eppendorf and incubated at 37° C. for 2 hr, while vortexing every 20 min. After the 37° C. incubation, the tissue contents of the Eppendorfs were poured into nylon mesh covered 15 ml Eppendorf tubes. The 1.5 ml Eppendorf tubes were washed with PBS and poured again into their respective nylon mesh covered Eppendorfs, in order to minimize sample loss. The nylon mesh covered Eppendorfs were centrifuged at 750 r.p.m.×10 min and the supernatant was removed with a pipette. Depending on the size of the pellet, between 0.5-2 ml of PBS was added to dilute the cellular specimen.

Cytospin slides were prepared from the 15 ml Eppendorf tubes. The concentration of the 15 ml Eppendorfs were adjusted in accordance with microscopic analysis of the cytospin slides. If too many cells were present in the field of view, then the Eppendorf tubes were diluted subjectively with 0.1 ml aliquots of PBS. If too few were present in the field of view, then the Eppendorf tubes were re-centrifuged and an estimated amount of supernatant was removed. After appropriate concentration adjustments, all cytospin slides were placed in a FISH fixative solution (3 parts methanol: 1 part acetic acid) for 20 min. Slides were stored in a –20° C. freezer.

Growth of BAC and Isolation of RPL 14 Template. A colony was inoculated with a 10 ml culture containing 1.5 ml LB+12.5 µg/ml chloramphenicol. It was grown overnight at 37° C., while shaking at 200 r.p.m. The culture was transferred to a 1.5 ml mirofuge tube. The cells were pelleted at full speed in a microfuge for 30 sec and the supernatant was removed. The cell pellet was thoroughly resuspended in 100 µl chilled Solution I using a Pipetman. 200 µl of freshly prepared Solution II was added to the tubes and they were then placed on ice. Each tube was mixed 8-10 times via inversion and returned to the ice. The cells lysed and the solution grew clear and viscous. Next, 150 µl of Solution III was added. The tubes were mixed by inversion 8-10 times and returned to the ice. The addition of solution III caused the formation of a flocculent precipitate. The tubes were centrifuged for 6 min at room temperature at full speed in a microfuge. The supernatant was transferred to a new microfuge tube. Any visible debris that was transferred was removed with a toothpick or pipet tip. The DNA was precipitated by adding 1 ml room temperature 100% ethanol and centrifuged for 6 min at room temperature in a microfuge. The supernatant was carefully removed and the DNA pellet was washed briefly in 70% ethanol. The pellet was air dried briefly (approximately 10 min) before being dissolved in an appropriate volume of TE buffer.

Preparation of 3p21.3 DNA Probe. The genomic clone of the gene was isolated from the CITB human BAC (bacterial artificial chromosomes) DNA library pools (Research genetics, Huntsville, AL0 using PCR technique with a specific 3p21.3 gene primer. Genomic DNA was isolated from this gene by growing the positive BAC clone and isolated gene RPL 14 genomic DNA using a Qiagen Plasmin Kit and following the manufactures directions. The gene DNA sequence was confirmed by using PCR with the same gene primer. Localization of the RPL14 gene on chromosome 3 was confirmed by using normal metaphase FISH. Digoxigen is added to the probed before denaturization of the slides, and follows the procedure in the Boehringer Mannheim Biochemicals kit. The 3p21.3 template DNA isolated from BAC clones was added to a cocktail of 36.5 ul distilled H₂O, 5 ul A4, 1 ul Digoxigenin-11-dUTP, 1 ul DNA polymerase-1, and 4.0 ul of 10× Enzyme mix. The final cocktail was incubated in a 15° C. water bath for 75 min. The enzymatic reaction was stopped via incubation of the cocktail in a 75° C. water bath for 15 min.

The efficiency of these probe depended on its size parameters. Using a 100 by DNA ladder marker and gel electrophoresis, the inventors could ensure that the 3p21.3 probe was between 200-1000 by size. The marker lane of the gel contained a 10 ul loaded sample: 1 ul 100 by DNA ladder, 2 ul loading buffer, 7 ul 1×TAE. The 3p21.3 lane of the gel contained a 10 ul loaded sample: 6 ul 3p21.3 DNA, 2 ul loading buffer, 7 ul 1×TAE. If the banding patterns of the gel showed the p4robe to be between 200-100 bp, then the 3p21.3 DAN probe would be ready for precipitation.

Precipitation of 3p21.3 DNA Probe. The probes are precipitated and bound with a fluorophore using a Nick Translation system (Life Technologies) following the specifications supplied by the manufacturer. 30 ul 3p21.3 DNA probe was added to 8.0 ul human Cot-I DNA, 1.0 ul placenta DNA, 3.9 ul NaAoc., and 86 ul 100% EtOH. The cocktail was vortexed and briefly centrifuged. It was stored in a −70° C. freezer for 15 min. Next, it was centrifuged in a temperature controlled chamber at 4° C. for 20 min×136,000 r.p.m. The resulting DNA pellet was air dried for 20 min and dissolved in 60 ul of hybridization buffer. Each slide prepared for FISH analysis requires 10 ul of hybridization buffer. To the hybridization buffer, 4 ul CEP 3 probe (spectrum orange) was added. The final solution was denatured in a 75° C. water bath for 5 min and then placed in a 37° C. water bath for 30 min.

FISH Method. Slides were pretreated in a series of 0.1 N HCI-0.2% Triton-X100 in 2×SSC (15 min RT[1], Vibra[2]) 2×SSC (2 min, RT, Vibra), 1×PBS (2 min, RT, Vibra), 1% Formaldehyde (2 min, RT, Vibra), 1% Formaldehyde (4 min RT, No Vibra), 1×PBS ((2 min, RT, Vibra), and 2×SSC ((2 min, RT, Vibra). Next, they were denatured in 70% formamide/2×SSC, pH 7.3 for 5 min in a 74° C. water bath. Trial and error showed that a temperature of 74° C. was critical for the production of quality slides for FISH. After denaturation, the slides were dehydrated in a cold alcohol series. They wee then subjected to a protease K digestion at 37° C. for 9 min and dehydrated again in a cold alcohol series. After air drying the slides, 10 ul of the 3p21.3 probe prepared in step 2.5 was applied to each slide. They were covered with glass cover slips, sealed with rubber cement, and allowed to hybridize overnight at 37° C.

Post-washing and Immunohistochemical Labeling. After overnight hybridization, post-hybridization washes occurred in three stages with two stages of antibody labeling in between the washes. The first wash consisted of three rinses in 50% Formamide/2×SSC at 45° C. for 10 min. each, two rinses in 2×SSC at 45° C. for 10 min. each, and one rinse 2×SSC at room temperature for 10 min. The slides were then blocked with 50 ul/slide 4×SSC+1% BSA blocking solution for 5 min. Afterwards, the primary antibody was diluted in a 1:20 ratio with the blocking solution and 50 ul was added per slide for 30 min in the dark. The slides were covered with paraffin cover slips to concentrate the blocking and antibody solutions over the cellular areas. The second wash consisted of one rinse in 4×SSC at RT for 10 min., one rinse in 4×SSC+1% Triton at RT for 10 min., one rinse in 4×SSC at RT for 10 min, and one rinse in PN at RT for 10 min. The slides wee then blocked again and labeled with the secondary antibody, which was prepared in a 1:100 ratio with the blocking solution. The labeling reaction was permitted to occur for 60 min. in the dark. The final wash consisted of three rinses in PN at RT for 10 min. each. Interphase cells wee counterstained with 1 ug/ml DAPI containing antifade solution. Ten microliters of DAPI counterstain were added to each slide.

Visualization and Scoring of FISH Signals. Hybridization sites were analyzed using Nikon microscopes equipped with appropriate filter sets for visualizing spectrum green and orange as well as DAPI counterstain. At 100 nuclei from each slide were scored using a triple filter. Each cell was scored individually for the number of RPL 14 signals (spectrum green) and the number of corresponding CEP3 (spectrum orange) signals. To avoid misinterpretation due to inefficient hybridization, cells were counted only if at least one bright CEP3 signal and one bright RPL14 signal were present to avoid false monosomies or deletions due to insufficient hybridization efficiency. Only non-overlapping, intact nuclei were scored. Split centromere signals were counted as one, and minor centromere signals wee disregarded. The inventors used Mantle Cell Lymphoma cells as a negative control.

TABLE 1

Lung Cancer Patients Deletion Rates of the 3p21.3 probe containing RPL14, CD39L3, PMGM, and GC20 gene and Patient Survival

|  | Deletion Percent | Expired |
| --- | --- | --- |
| Adenocarcinoma Cases | | |
| 1a | 3% | dead |
| 1b | 10% | |
| 2a | 2% | alive |
| 2b | 11% | |
| 3a | 8% | alive |
| 3b | 16% | |
| 4 | 50% | dead |
| 5 | 2% | dead |
| 6a | 14% | alive |
| 6b | 30% | |
| 7 | 44% | dead |
| Squamous Cases | | |
| 8a | 4% | dead |
| 8b | 44% | |
| 9a | 8% | alive |
| 9b | 64% | |
| 10a | 6% | alive |
| 10b | 8% | |
| 11 | 58% | dead |
| 12a | 6% | alive |
| 12b | 10% | |

Discussion. Table 1 provides an organized view of 12 patents suffering form lung cancer. The patients were separated into two different groups: those with adenocarcinoma and those with squamous cell carcinoma. For example, 3b represents cells isolated from a bronchous tumor via punch biopsies of paraffin embedded tissue blocks. The partner number 3a represents cells isolated from the same paraffin block, but from a nontumorous bronchous. Next, two types of cell samples were isolated per patient. Using FISH techniques directed to the Centromere 3 and the RPL14 gene of dissociated cells, the inventors were able to determine the deletion rate of the RPL14 gene in all patients. Initial data shows a promising correlation between the deletion percentage and survival of a patient.

Example 2

Retrospective Study of Lung Cancer Using 3p21.3 Gene Probe and FISH Detection

From an initial population of 200 patients studied retrospectively with Stage I lung cancer (culled from >13,000 patient files 1987-1988) the inventors identified 100 patients who had relapsed or died within 5 years. Additionally the inventors obtained archival bronchial tissue from 100 patients with lung tissue removed for reasons other than cancer which formed the basis of the control group. A detailed demographic history including smoking status, occupational history and family history of cancer was obtained for each patient.

The RPL14 gene probe (located on 3p21.3). Specific primer was designed based on the gene sequence with Electronic-PCR software. The genomic clone of the gene was isolated from the CITB human BAC DNA library pools (Research genetics, Huntsville, Ala.) using PCR technique with this specific gene primer.

Isolation of genomic DNA of 3p21.3. Growth of the positive BAC clone and isolated gene RPL14 genomic DNA using Qiagen Plasmid Kit as instructed by the manufacture. The gene DNA sequence was confirmed by using PCR with the same gene primer. Localization of the RPL14 gene on chromosome 3 was confirmed by using normal metaphase FISH. Preparation of specific gene FISH probes were prepared using a Nick Translation System (Life Technologies) as instructed by the manufacturer. If the banding patterns of the gel showed the probe to be between 200-1000 bp, then the probe would be ready for precipitation.

The BAC clone that contained genomic sequences that have the highest frequency of deletion at 10q region in tumor cell lines was selected. The DNA of this BAC clone isolation and probes labeling procedure were performed as above.

Tissue samples. Punch biopsies of histologically representative cancerous lung tissue and adjacent normal or histologically abnormal bronchial epithelial tissues were performed on paraffin embedded blocks. Resulting tissue sections were digested to obtain cell dissociation of interphase nuclei according to the Hedley technique. A subset of cases had imprints obtained form tumor and adjacent bronchus. Cells were fixed in FISH fixative which is Carnoy's solution (methanol and acetic acid in a 3:1 ratio).

FISH Studies. Dual color FISH studies were performed with the Spectrum Orange centromeric probes for chromosome 3 (CEP 3) (Vysis) and digoxigenin labeled specific RLP 14 gene or the Spectrum Orange centromeric probes for chromosome 10 (CEP 10) (Vysis) and Digoxigenin labeled specific 10q22 probes. CEP 3 or 10 probes were used as control probes respectively.

Slides were denatured in 70% formamide at 73° C. for 5 min. A mix of probes were denatured for 5 min at 75° C. and then applied to slides. After overnight hybridization at 37° C., post-hybridization washing were as follows: 50% Formamdie/2×SSC at 45° C. for 5 min. Digoxigenin labeled specific gene or 10q22 probes are detected by FITC conjugated sheep antidigoxigenin.

Interphases were counterstained with DAPI or PI counterstaining antifade solution. Hybridization sites were analyzed using Nikon microscopes equipped with the appropriate filter sets for visualizing spectrum green or orange as well as nuclei Counterstain. At least 200 nuclei with signals from each probe were scored using a triple filter. Slides were analyzed only if 80% of the cells were interpretable in the field of view. Only non-overlapping, intact nuclei were scored. Split centromeric signals (distance between two signals was equal or less than 0.5 um) were counted as one, and minor centromeric signals were disregarded. Normal lymphocytes were used as external control Deletion (%) was defined percent of cells with fewer signals of specific probe than signals of CEP3 or CEP10 in 200 cells counted.

Results. To date, the inventors have examined numerous dissociated tumors with their adjacent bronchi as well as numerous controls. Based on the results using DNA probes from 3p and 10q, the inventors have shown that the probes most likely are detecting tumor suppressor genes that are lost early on in tumorigenesis, are associated with smoking and appear to predict for the development of non-small cell lung cancer as well as for its overall survival. In addition, the inventors have shown that non-smokers who develop lung cancer have much higher rates of deletions, higher even than smokers (FIG. 1-2) and that these results are statistically significant ($p<0.001$).

Figure 2:
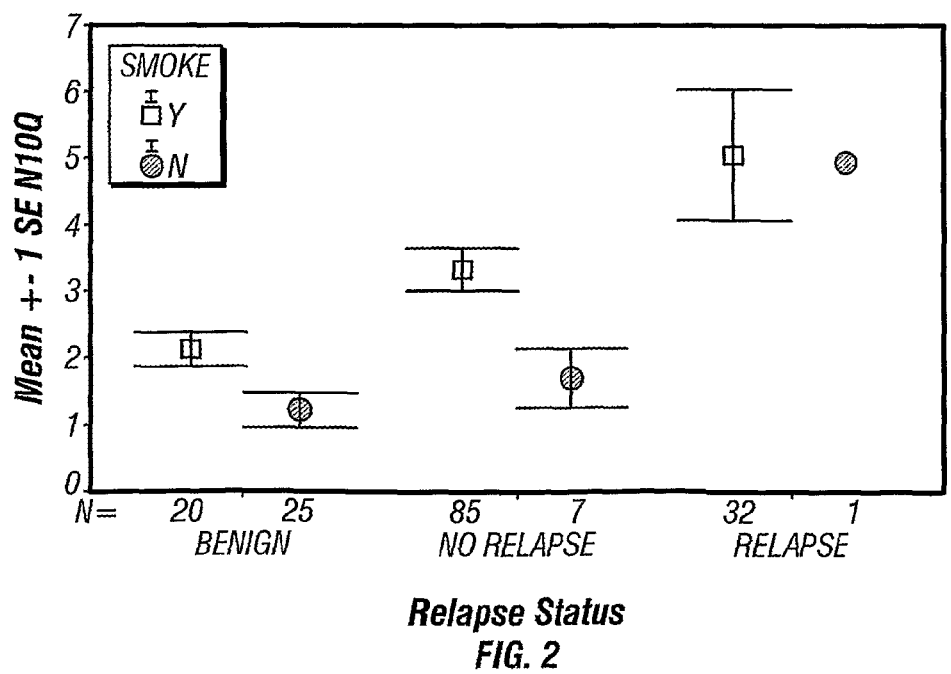
Figure 3:
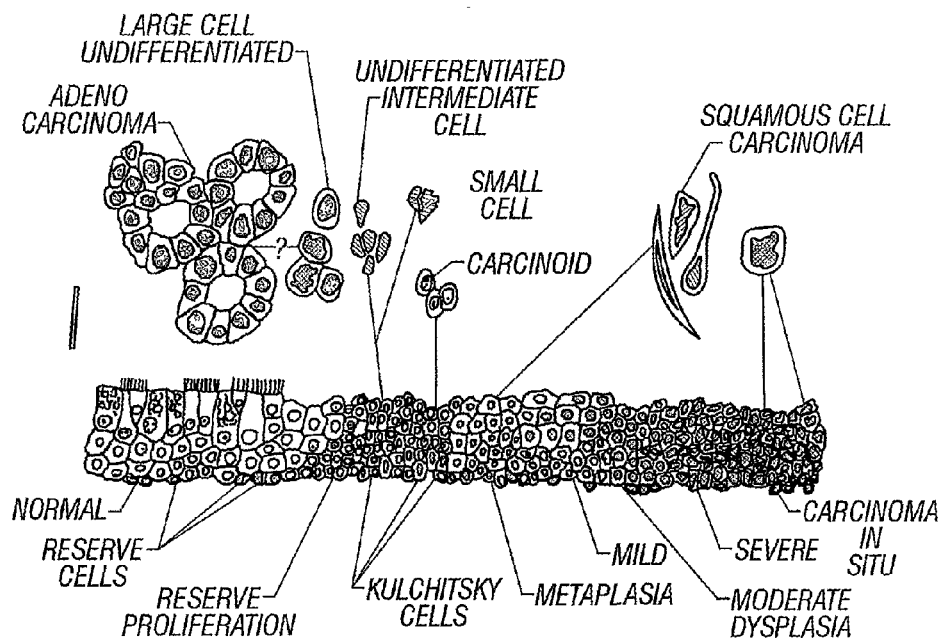

FIG. 1 and FIG. 2 show the 3p21 and 10q22 deletion rates in adjacent bronchial epithelial cells of patients with benign lung disease, patients who developed stage 1 non-small cell cancer that did not relapse, and patients with stage 1 non-small cell cancer with relapse. Note that patients who relapsed had a much higher level of deletions than those patients who did not relapse, regardless of smoking status.

3p and 10q deletions were frequently expressed in lung tumors and showed no correlation with relapse, however the presence of 3p and 10q abnormalities in adjacent bronchial tissue was strongly correlated with relapse (0.09, and 0.0279) and survival ($p=0.0348$). Therefore, the probes may be useful markers in smoking-related damaged epithelium for risk assessment and for monitoring the efficiency of chemopreventive regimes.

Example 3

Lung Cancer Susceptibility in Former Heavy Smokers

A subset of bronchial lavages from former heavy smokers who had quit for an average of 6 years with median pack year history of 46 years was studied for lung cancer susceptibility. The study patients have surveillance bronchoscopy followed by blind biopsies of main bronchi from both lungs. Following this, a bronchial wash was performed, and triaged. Even though all these patients had quit smoking (average 6 years previously) most showed significant deletions for the 3p21 or the 10q22 FISH probes in bronchial wash specimens, indicating that in genetically susceptible individuals molecular defects appear to be persistent and are not related to the number of pack years.

Example 4

Serial Dilution of Tumor Cells

Figure 4:
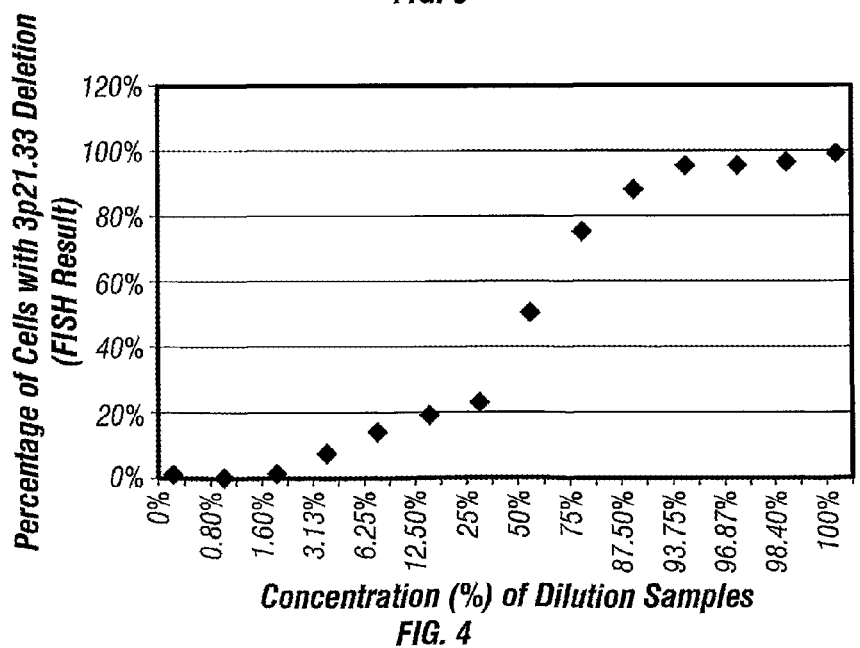
Figure 5:
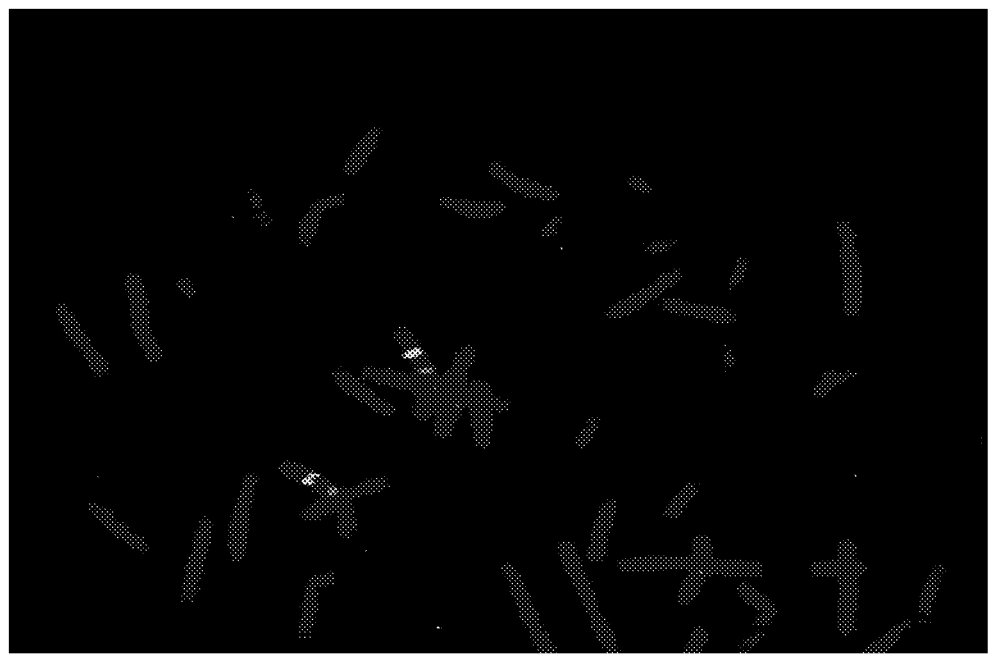
Figure 6:
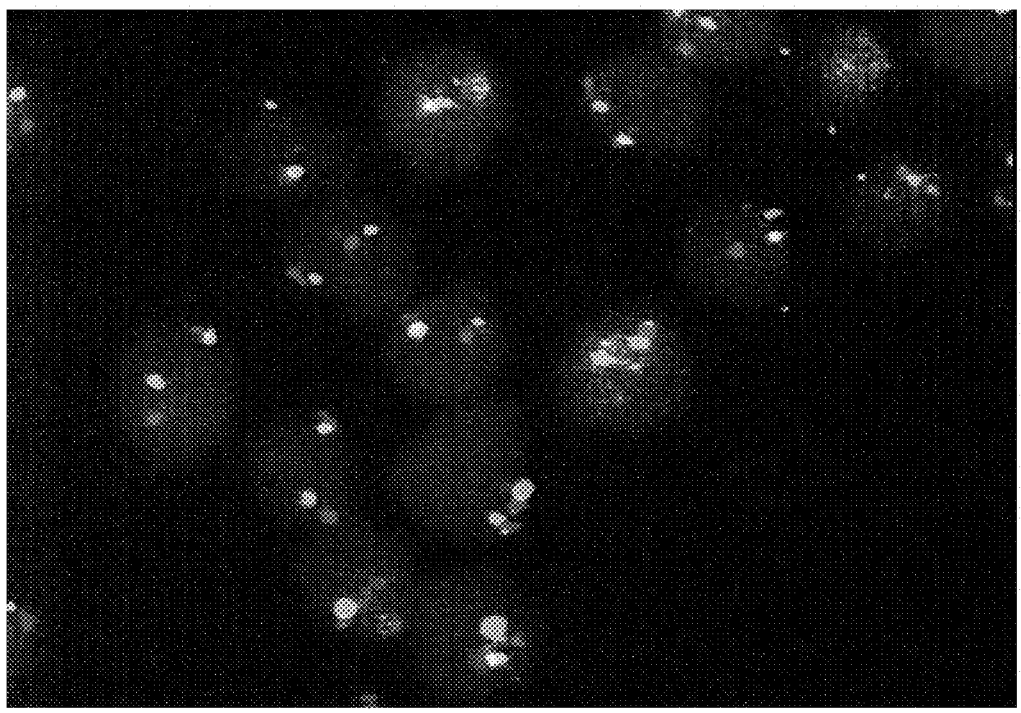
Figure 7:
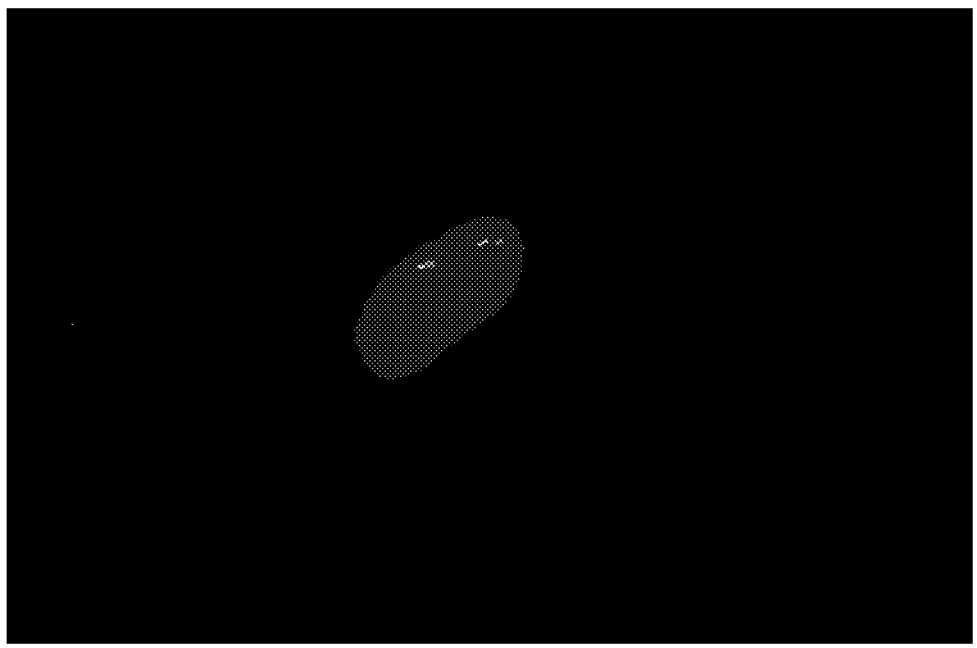
Figure 8:
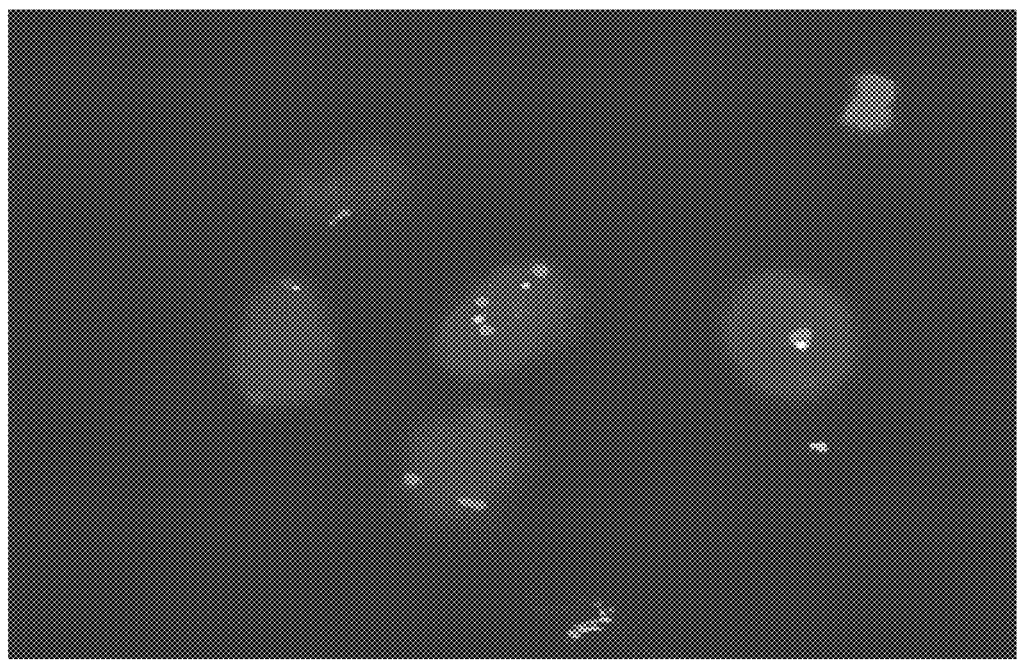
Figure 9:
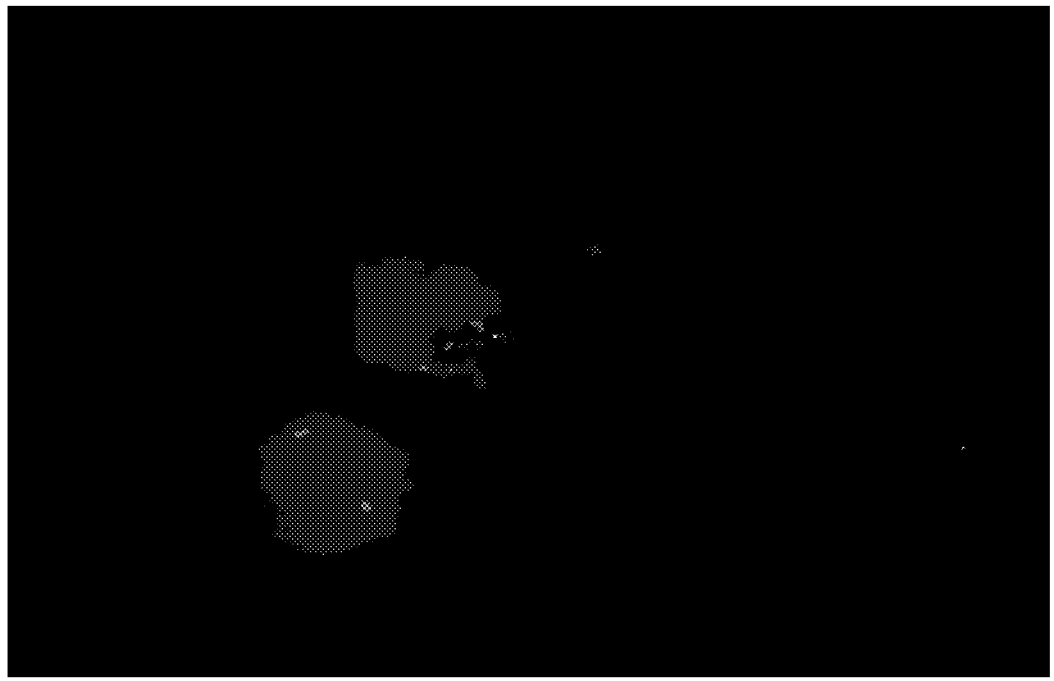

To detect how low concentration of tumor cells in the bronchial washing sample can be detected and the actual number and distribution of the gene in individual morphological cells, a serial dilution was done for evaluating the sensitivity of the 3p21.33 FISH probe. This test was also for quality control purpose. Two cell lines were used for the serial dilution experiment. H-1792 lung adenocarcinoma cell line was obtained from ATCC, the cell line exhibited cytogentic abnormalities including trisome chromosome 3 and 3p21.33 deletion. By FISH analysis, the cell demonstrated that over 100% of the interphases had 3 signals of CEP3 in contrast to 2 signals of 3p21.33 with 3p21.33/CEP11 probes. The normal bronchial epithelial cell was derived from a normal individual, showing normal number and structure of chromosome 3. H-1792 cells were mixed with same number of normal epithelial to dilute H-1792 cells to 50%. A serials of dilution was performed to further dilute H-1792 cell to 25%, 12.5%, 6.3%, 3.1%, 1.6%, 0.8%. The slides were made by cytospin preparations and randomized before hybridization. After hybridization and post washing, the percentage of cells with deletion of 3p12.33 signals were counted and compared with the projected values, as shown in FIG. 4.

Results of the serial dilution experiment demonstrated that the dilution concentration was positively related to the percentage of 3p21.33 deletion cells detected by FISH. However, when tumor cell line were diluted to a concentration ≦3.1%, it was not possible to identify 3p21.33 deletion cells, suggesting that the sensitivity of the probe or the lowest concentration of positive cells detected by the probe in bronchial washings was 3.1%.

Example 5

Progression of GC20 Study

After narrowing down the critical gene region in 3p21, the novel gene SUI1/GC20 (SEQ ID NO: 7) was identified in the region. SUI1/GC20 is a homolog of the SUI1 gene, which is a superfamily consisting of a growing number of proteins; SUI1 is a 113 amino-acid polypeptide similar to the protein from various different species. Primarily, the SUI1 gene product was believed to be a monitor translational accuracy protein by recognition of the protein synthesis initiation codon. Recent studies demonstrated that the SUI1 protein has a role in the nonsense-mediated mRNA decay pathway, by which cells have evolved elaborate mechanisms to rid themselves of aberrant proteins and transcripts. Identification of a stress-inducible cDNA of SUI1 suggested that modulation of translation initiation occurs during cellular stress and may represent an important adaptive response to genotoxin (e.g., tobacco) as well as endoplasmic reticular stress. SUI1 was expressed in normal liver but not in liver carcinoma cells. Introduction of SUI1 into liver carcinoma cells inhibited cell growth in vitro and partially inhibited tumor formation in nude mice. It is rational to suggest, therefore, proteins of the SUIL family possess tumor-suppressing properties and may represent a primary event, rather than a consequence, of tumorigenesis. Furthermore, since deletion of 3p21.3 was found by others to be the earliest acquired genetic changes in the pathogenesis of lung cancer, inventors also found that SUI1/GC20 transcript was diminished in all lung cancer cell lines tested by reverse transcription-PCR(RT-PCR). Inventors have cloned the full-length cDNA of SUI1/GC20 into a constitutive (pcDNA3.1/GS) with the C-terminal V5 epitope and polyhistidine (6×His) tag (SEQ ID NO: 9). The first four nucleic acids of SEQ ID NO: 9, "cacc" were added to the insert before the ATG by including the sequence in the forward primer (SEQ ID NO: 11), in order to conform to the to the consensus Kozak sequence for optimal translation initiation. The reverse primer is given in SEQ ID NO: 10 The last 102 nucleic acids of SEQ ID NO: 9 is not part of the insert, but is derived from the vector pcDNA3.1/GS, and codes for the V5/6x His tag.

The non-small cell lung cancer cell line H1972 was transfected with the full-length cDNA of SUI1/GC20 (SEQ ID NO: 9), resulting in H-1972 pcDNA3.1/GC20 or with the vector pcDNA3.1/GS (resulting in H-1972 pcDNA3.1) as control. Protein expression of GC20 was detected in the H-1972 pcDNA3.1/GC20 cells, but not in control cells. The growth of H-1972 pcDNA3.1/GC20 cells in serum-containing medium was significantly slower than that of H-1972 or the vector-transfected control H-1972 pcDNA3.1.

Studying the molecular genetic mechanisms by which SUI1/GC20 is inactivated can be done to characterize the gene. Analyze of the function of the gene can also be used to demonstrate its ability to inhibit cell growth and suppress tumorgenicity. As results of these studies, there is a better understanding of the tumorigenesis of tobacco-related lung cancer and the clinical biomarkers useful for its early detection and risk assessment.

Example 6

FISH Studies on Bronchial Wash Specimens from Patients with Benign, Atypical and Malignant Cytology Using a 3p21.3 DNA Probe Bronchial wash specimens were tested for deletions of 3p21.3 by FISH using the locus-specific probe for 3p21.3 together with a centromeric probe for chromosome 3 as control. Inventors tested patients with non-small cell bronchogenic carcinoma, and patients on a chemopreventive protocol who demonstrated by cytology metaplasia, reserve cell hyperplasia or no abnormality. Also, the presence of the 3p deletion was correlated with the number of pack-years of smoking or tobacco-use.

Negative Cytology 7 cases with negative cytology showed levels of deletions of 3p21.3 between 0%-13% (mean 7.2±0.05) when tested with the 3p21.3 probe. The highest level of deletion was associated with a 122.5 pack year history of smoking. Interestingly, this high level of deletion was noted in two specimens, 6 months apart, from the same patient, indicating that there is a consistent deletion that did not response to fenretinamide (or cis-retinoic acid) therapy that was used as a chemopreventive agent.

Atypical Cytology There were 6 cases with cytological evidence of either reserve cell hyperplasia or squamous metaplasia/atypical metaplasia. The highest level of deletion was noted in a 90-pack year smoker. The deletions ranged from 7% to 15% (mean=10.5%±0.036).

Carcinoma In the third category of patients with cytological evidence of carcinoma (2 squamous carcinoma, 1 adenocarcinoma), the mean percent deletion was 17±0.13 (range: 8%-23%).

Results These results showed that in patients without evidence of lung cancer/squamous atypia, who had a history of smoking, a deletion of 3p21.3 existed that roughly paralleled the number of pack years smoked indicating that this deletion may occur secondarily to exposure to tobacco smoke, and also may be an early event in neoplastic transformation. None of these patients have yet to evidence clinical or straight chest X-ray evidence of lung cancer, however, those with the highest levels of deletion may be at high risk to develop neoplasia.

In patients with atypia as manifested by squamous metaplasia or atypia, the level of deletion was higher than in the negative group, with the highest levels of deletion noted in patients with carcinoma.

The results also correspond with previous studies with 3p21.3 probe for chromosomal aberrations in microdissected lung carcinomas and adjacent "normal" bronchial cells. Genetic instability is a very early event in tumorigenesis and chromosomal numerical abnormalities are associated with smoking. 3p21.3 deletions occurred more frequently in the lung tumors and adjacent bronchi of the patients who smoked than in control lung tissue from patients who did not smoke. Smoking may cause molecular damage much earlier than the corresponding manifestation of neoplasia at a morphologic level. Smoking is a major etiologic factor for the development of lung cancer and based on the studies presented herein, the loss of 3p21.3 is an early event in the tumorigenesis of lung cancer.

The 3p21.3 probe will be a useful marker in monitoring smoking-related target epithelia to measure risk assessment and for monitoring the efficiency of chemo-prevention therapy in high-risk former or current smokers.

TABLE 2

Results of FISH Studies on Bronchial Wash Specimens from Patients with Benign, Atypical and Malignant Cytology Using a 3p21.3 DNA Probe.

| BW # | MDA # | DATE Received | SMOKE HX (PackYears) | DIAGNOSIS | 3pFISH |
|---|---|---|---|---|---|
| Benign | | | | | |
| 87 | 228891 | May 11, 2000 | 67.5 | No slide | 0% |
| 179 | 398860 | Oct. 12, 2000 | 122.5 | Negative | 12% |
| 212 | 398860 | Jan. 12, 2001 | 122.5 | Negative | 13% |
| 247 | 451844 | May 1, 2001 | 45 | Negative | 12% |
| 249 | 424531 | May 4, 2001 | 44 | Negative | 5% |
| 257 | 459858 | Jun. 26, 2001 | 39 | Negative | 8% |
| 258 | 458362 | Jul. 12, 2001 | 26 | Negative | 1% |
| Atypia | | | | | |
| 31 | 413570 | Jan. 19, 2000 | 87.5 | Metaplasia | 12% |
| 146 | 385669 | Sep. 1, 2000 | Non-Smoker | Metaplasia | 8% |
| 243 | 475347 | Apr. 26, 2001 | 38 | Metaplasia | 14% |
| 244 | 474853 | Apr. 26, 2001 | 30 | Metaplasia | 7% |
| 246 | 475666 | Apr. 27, 2001 | 90 | Metaplasia | 15% |
| 256 | 429515 | Jun. 8, 2001 | 75 | reserve cell hyperplasia | 7% |
| Malignant | | | | | |
| 252 | 404860 | May 8, 2001 | 60 | Sq. CA | 11% |
| 127 | 358000 | Aug. 3, 2000 | Non-Smoker | Sq. CA | 8% |
| 210 | 406098 | Jan. 10, 2001 | Non-Smoker | Ad. CA | 32 |

Example 7

Sensitivity of the 3p21.33 FISH Probe in Detecting Lung Cancer Cells in Bronchial Wash Specimens It was hypothesized that deletions of 3p.21.33 may be detected early on in carcinogenesis, and may thus have the potential to predict a patient's predisposition towards developing either primary lung cancer or a relapse thereof. The purpose of this study was to explore the efficacy of the FISH test, specifically the sensitivity of the 3p21.33 probe, for determining 3p21.33 deletions in interphase cells from patients' bronchial samples with the aim of developing a method for determining genetic predisposition to lung cancer. The sensitivity of the outcome depended on the visibility of the 3p21.33 gene loci as well as the ability to detect deletions of the 3p21.33 locus in the malignant cell lines compared to the admixed normal bronchial cells.

Cell Samples and Slides The tumor cells in this study were obtained from an H-1792 lung adenocarcinoma cell line obtained from ATCC, which exhibited cytogenic abnormalities including trisomy of chromosome 3 and 3p21.33 deletion. These cells were separated and harvested from culture bottles and diluted from a concentration of $2.52 \times 10^6$ cells per ml to $7.14 \times 10^5$ cells per ml using PBS buffer. Normal bronchial epithelial cells, showing normal numbers and structure for chromosome 3, were acquired from the bronchial wash of a normal individual at a concentration of $7.14 \times 10^5$ cells per ml. The cancer cell sample was diluted by the normal cells to concentrations of 0%, 0.8%, 1.6%, 3.13%, 6.25%, 12.5%, 25%, 50%, 75%, 87.5%, 93.75%, 96.8%, 98.4%, and 100% and transferred onto individual slides using a cytospin preparation.

Nick Translation The DNA probe used to identify the 3p21.33 gene was created using nick translation, a widely used method for its ease in controlling fragment size (Wilkinson, 1998) Digoxigenin enzyme, which is able to be detected with antibodies, was used to cut 3p DNA (Andreeff et al., 1999). The probe was tested using gel electrophoresis to ensure a length of 200-500 kilobase pairs. CEP3 probe (chromosome 3 centromere) was premixed and provided by a commercial company (Vysis, Downers Grove, Ill.).

FISH Method The 3p21.33 probe was precipitated by mixing with human cot-1 DNA (Vysis, Downers Grove, Ill.), human placenta DNA (Sigma, La Jolla, Calif.), NaOAcetate, and 100%-20 ethanol, incubated at $-80°$ C. for 15 minutes, and centrifuged for 20 minutes at $4°$ C. The remaining pellet was dissolved in hybridization buffer (Vysis, Downers Grove, Ill.) at room temperature, at 10 µl per slide, and the centromeric probe was added. The probe was placed in a $75°$ C. water bath for 5 minutes and then transferred to a $37°$ C. water bath for 20 minutes. At the same time, the slides to be tested were placed into a 70% Formamide/SSC solution for 3 to 4 minutes to denature the DNA and subsequently placed into a series of cold ethanol jars in order to permeabilize the cells by removing the lipid membranes (Wilkinson, 1998). 10 µl of the probe was then pipetted onto each slide and put into a humidity box to incubate overnight at $37°$ C. The following day, the slides were first placed into 3 jars of 50% Formamide/2×SSC at $45°$ C. for 10 minutes each and then into a jar of 2×SSC for 10 minutes at $45°$ C. as well. The slides were blocked for five minutes using 4×SSC/BSA and then covered with the first antibody (anti-digoxigenin) and placed in a humidity box for an hour. This was followed by a series of TNT buffer washings. Once again the blocking procedure was performed before the second antibody was placed on the slides for another hour. The slides were washed again with TNT buffer. Lastly, 10 µl of DAPI was added to the slides to stain the nucleus of each cell.

Visualization and Counting of FISH Signals The hybridized slides were examined utilizing a Labophot-2 microscope (Nikon, Tokyo, Japan) under filters for visualizing green, orange, and DAPI fluorescence signals (FIGS. 5-9). One hundred cells were selected for analysis from each dilution, and were counted only if the entire nucleus was distinct and intact. To avoid misinterpretations owing to false monosomies or deletions due to insufficient hybridization, nuclei were counted only if at least one bright CEP3 signal (orange) and one bright 3p21.33 signal (green) were present. The numbers of orange signals versus green signals were counted and recorded individually for each chosen cell. A particular cell was deemed a normal epithelial cell if it had an equal number of green and orange signals, signifying that there was one 3p.21.33 gene per centromere on the chromosomes. In contrast, cells were identified as tumor cells if they possessed fewer green signals than orange signals, proving that there, indeed, was a deletion of the 3p21.33 gene within its genomic makeup.

Results and Discussion Typically, normal epithelial cells displayed 2 orange and 2 green signals, whereas tumor cells showed 3 orange and 2 green signals (FIGS. 5-9). Data indicates that the baseline sensitivity for FISH detection of deletions of 3p21.33 is 3.13% (see Example 4), this places high hopes for early detection of the development lung cancer, recurrence, or metastasis. With extended studies, the FISH probe for 3p21.33 can be established and widely used as a useful and reliable marker for assessing lung cancer and, perhaps, further utilizing and improving methods like fine needle aspiration in conjunction with the FISH method. This study also lays the baseline for future studies and for the monitoring of preneoplastic or neoplastic events and may be used as a surrogate intermediate biomarker in chemoprevention techniques in lung cancer.

Example 8

Statistical Analysis of 10Q Probe

Figure 10:
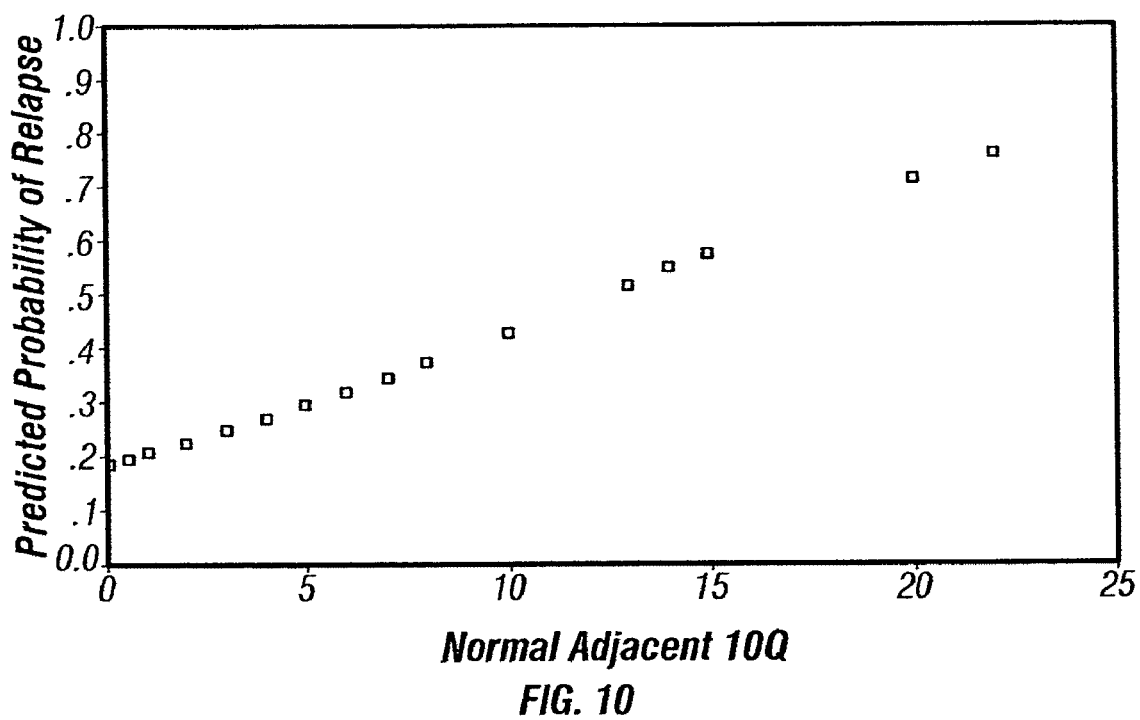
Figure 11:
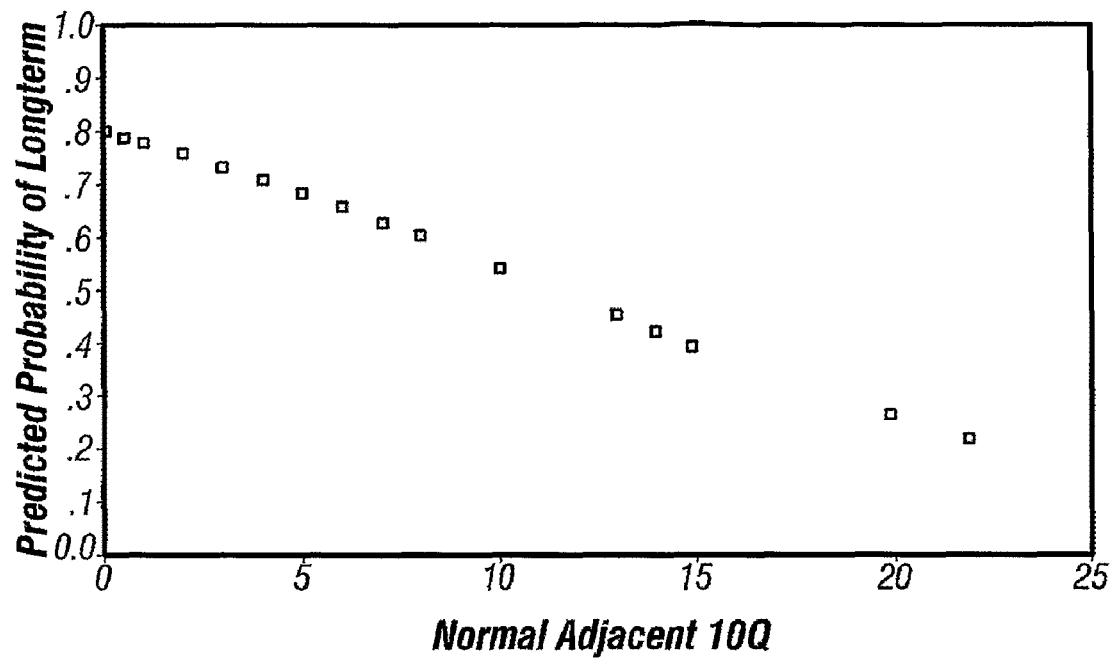

FIG. 10 and FIG. 11 provide a predicted probability of relapse and long term survival for patients. Using data from 96 patients, the deletion of 10Q in bronchial epithelial cells adjacent to the tumor cells is compared with both relapse (FIG. 10 and long term survival (FIG. 11). 10Q deletion is a significant predictor of relapse.

Figure 12:
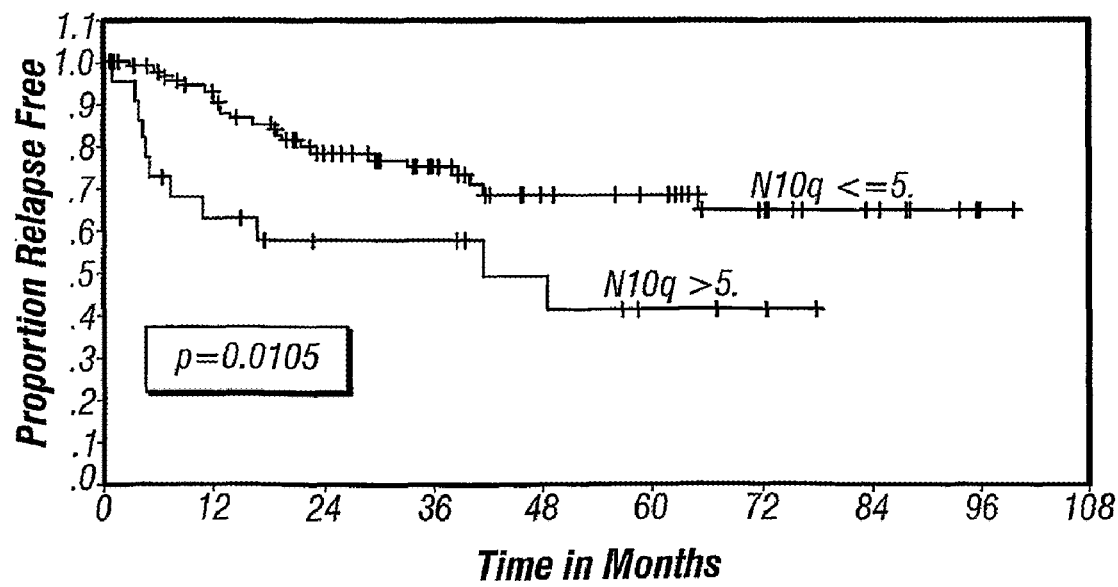
FIG. 12—Interval for Patients who are Relapse Free. The proportion of patients who are relapse free from 0 to 108 months for patients who have a N10q value >5 and N10q$\leq$5.

In FIG. 12, the proportion of patients who are relapse free at times ranging from 0 to 108 months is shown. The data is divided into a set of patients who have a N10q value of greater than 5 and patients who have a N10q value of less than or equal to 5. While about 40% of the patients with N10q>5 are relapse free after a long interval (5-7 years), over 60% of the patients with N10q≦5 are relapse free after the same time interval.

REFERENCES

The following references, to the extent that they provide exemplary procedural or other details supplementary to those set forth herein, are specifically incorporated herein by reference:

Wilkinson; D. G. *In Situ Hybridization: A Practical Approach*. New York, Oxford: 1998.
Andreeff, M. D., Ph.D., Michael, Pinkel, Ph.D., Daniel. *Introduction to Fluorescence in Situ Hybridization: Principles and Clinical Applications*. New York, Wily-Liss: 1999.
Alberola et al., *Proc. Annu. Mt. Am. Soc. Clin. Oncol.*, 14: A1094, 1995.
Auerbach et al., *N. Engl J. Med.*, 265: 253-267, 1961.
Ayabe et al., *Lung Cancer*, 11(3-4): 201-208, 1994.
Barinaga, *Science*, 271: 1233, 1996.
Brugal et al., *Method. Achiev. Exp. Pathol.*, (Karger, Basel) 11: 1-33, 1984.
Carcy et al., *JNCI*, 65: 1225-1230, 1980.
Carriaga et al., *Cancer*, 75: 406-421, 1995.
Cheon et al., *Yonsei Med. J.*, 34(4): 365-370, 1993.
Dalquen et al., *Virchows Archiv.*, 431(3): 13-179, 1997.
Dong et al., *Science*, 268: 884-886, 1995.
Ekins, R.; Chu, F. W., *Trends in Biotechnology*, 17: 217-218, 1999.
Fearon et al., *Science*, 247: 47-56, 1990.
Feder et al., *Cancer Genet. Cytogenet.*, 102: 25-31, 1998.
Feinstein et al., *Am. Rev. Repir. Dis.*, 101: 671-684, 1970.
Field et al., *Cancer Res.* 59: 2690, 1999.
Fodor et al., *Science*, 251:767-773, 1991.
Fontanini et al., *Cancer*, 70(6): 1520-7, 1992.
Frohman, M. A., In: *PCR PROTOCOLS: A GUIDE TO METHODS AND APPLICATIONS*, Academic Press, N.Y., 1990
Hacia et al., *Nature Genetics*, 14:441-447, 1996.
Hirano et al., *American J. Path.*, 144(2): 296-302, 1994.
Hirsh, *Manksgaard*, 1-78, 1983.
Holmstrom et al., *Anal. Biochem.* 209:278-283, 1993.
Hosoe et al., *Lung Cancer*, 10: 297, 1994.
Ichinose et al., *J. Surgical Oncology*, 46(1): 15-20, 1991.
Ihde, *Curr. Prob. Cancer*, 15: 65, 1991.
Kim et al., *Korean J. Intern Med.*, 11(2): 101-7, 1996.
Kwoh et al., *Proc. Nat. Acad. Sci. USA*, 86: 1173, 1989.
Licciardello et al., *Int. J. Radiat. Oncol. Bio. Phys.*, 17: 467-476, 1989.
Liewald et al., *Chirurg*, 63(3): 205-10, 1992.
Lifton, *Science*, 272: 676, 1996.
Macchiarini et al., *Proc Annu Mt. Am. Soc. Clin. Oncol.* 11: A995, 1992.
Miki et al., *Science* 266: 66-71, 1994.
Mitsudomi et al., *Clin. Cancer Res.*, 2(7): 1185-9, 1996.
Miyamoto et al., *Cancer Research*, 51(23pt1) 6346-50, 1991.
Morahan et al., *Science* 272: 1811, 1996.
Mrkve et al., *Anticancer Research*, 13(3): 571-8, 1993.
Muguerza et al., *World J. Surg.* 21(3): 323-329, 1997.
Naruke et al., *J. Thorac. Cardiovas Surg*, 96: 400, 1988.
Newton, C. R, et al. *Nucl. Acids Res.* 21:1155-1162 (1993).
Ohara et al., *Proc. Nat'l Acad. Sci.* USA, 86:5673-5677, 1989.
Pantel et al., *Proc. Annu Mt. Am. Soc. Clin. Oncol.*, 12: A941, 1993.
Papadimitrakopoulou et al., *Cancer and Metastasis Reviews*, 15: 53-76, 1996.
Pease et al., *Proc. Natl. Acad. Sci. USA*, 91:5022-5026, 1994.
Pence et al., *Archives of Surgery*, 128(12): 1382-1390, 1993.
Pignon et al., *Hum. Mutat.*, 3: 126-132, 1994.
R. Ekins and F. W. Chu, *Trends in Biotechnology*, 17: 217-218, 1999.
Rasmussen, et al., *Anal. Biochem*, 198:138-142, 1991.
Rice et al., *J. Thoracic Cardio. Surgery*, 106(2): 201-217, 1993.
Running. J. A. et al., *BioTechniques* 8:276-277, 1990.
Sahin et al., *Cancer*, 65(3): 530-7, 1990.
Saiki et al., *Science*, 239: 487-491, 1988.
Sambrook et al., (ed.), *Molecular Cloning*, Cold Spring Harbor Laboratory Press, Cold Spring Harbor, N.Y., 1989.
Satoh et al., *Mol. Carcinog.*, 7: 157, 1993.
Shiseki et al., *Genes Chromosomes Cancer*, 17(2): 71-7, 1996.
Shoemaker et al., *Nature Genetics* 14:450-456, 1996.
Shriver et al., *Mutat. Res.* 406(1): 9-23, 1998.
Sidransky et al., *Science*, 252: 706-709, 1991.
Siest et al., *J. Cellul. Biochem.*, 28/29: 64, 1997.
Slamon et al., *Science*, 244: 707-712, 1989.
Taparowsky et al., *Nature*, 300: 762-764, 1982.
Thiberville et al., *Cancer Research*, 55: 5133-5139, 1995.
Thiberville et al., *Int. J. Cancer*, 64: 371, 1995b.
Travis et al., *Cancer*, 75: 191-202, 1995.
Valdivieso et al., *Proc. Annu. Mt. Am. Soc. Clin. Oncol.*, 13: A1121, 1994.
Vallmer et al., *Hum. Pathol.*, 16: 247-252, 1985.
VanOijen et al., *Cancer Epidemiology, Biomarkesr & Prevention*, 9: 249, 2000.
Vo-Dinh, et al., *Anal. Chem.*, 66: 3379-3383, 1994.
Volm et al., *Versicherungsmedizin*, 41(1): 2-5, 1989.
Voravud, et al., *Cancer Research*, 53: 2874-2883, 1993.
Walker et al., *Nucleic Acids Res.* 20(7):1691-1696, 1992.
Wistuba et al., *Cancer Res.*, 60(7): 1949-60, 2000.
Wu et al., *Cancer Res.*, 58(8): 1605-8, 1998.
Yamaoka et al., *J. Japan Surgical Soc.*, 91(10): 1608-16, 1990.
Yanagisawa et al., *Cancer Research*, 56: 5579-5582, 1996.
Zou et al., *Clinical Cancer Research* 4: 1345-1355, 1998.

What is claimed is:

1. A method for identifying a subject at risk for the development of non-small cell lung cancer comprising:
   (a) obtaining a test sample from a human subject;
   (b) providing a 3p21 DNA probe selected from a CD39L3, PMGM, or GC20 gene probe;
   (c) contacting the probe with the test sample;
   (d) analyzing DNA from the test sample,
   (e) detecting a loss of heterozygosity in the hybridization of the probe to the DNA, as compared to a centromeric DNA probe for chromosome 3; and
   (f) identifying the subject at risk for the development of non-small cell lung cancer when loss of heterozygosity is detected.

2. The method of claim 1, wherein the method further comprises providing a RPL14 gene probe.

3. The method of claim 1, wherein the test sample comprises a surgical or biopsy specimen, a paraffin embedded tissue, a frozen tissue imprint, a sputum, esophageal brush, a fine needle aspiration, a buccal smear or a bronchial lavage.

4. The method of claim 1, wherein the subject is a smoker.

5. The method of claim 1, wherein the subject is a former smoker.

6. The method of claim 1, wherein the subject is a non-smoker.

7. The method of claim 1, wherein the test sample comes from the subject who has not previously been diagnosed with cancer.

8. The method of claim 1, wherein the probe is labeled with fluorophores.

9. The method of claim 1, wherein probe is labeled with digoxigenin.

10. The method of claim 1, wherein size of the probe is between 1000 and 2000 base pairs.

11. The method in claim 1, further comprising performing a spiral CT-scan.

12. The method of claim 1, wherein the method is used to identify subjects who need an intensive follow-up protocol.

13. The method of claim 1, wherein the probes are used to identify subjects who are suitable for novel investigational therapeutic approaches.

14. The method of claim 1, wherein said centromeric probe is labeled with a fluorophore.

15. The method of claim 14 wherein said centromeric probe is labeled with spectrum orange.

16. The method of claim 1, wherein said centromeric probe is a chromosome 3 stable marker.

17. The method of claim 16, wherein said centromeric probe is Centromere 3 (CEP 3).

18. The method of claim 1, wherein analyzing comprises using FISH.

19. A method for predicting the development of non-small cell carcinoma in a subject comprising:
   (a) obtaining a lung test sample from a human subject;
   (b) providing a 3p21 DNA probe selected from a CD39L3, PMGM, or GC20 gene probe;
   (c) contacting the probe with the test sample;
   (d) analyzing DNA from the test sample,
   (e) detecting a loss of heterozygosity in the hybridization of the probe to the DNA, as compared to a centromeric DNA probe for chromosome 3; and
   (f) predicting the development of non-small cell carcinoma in the subject.

20. The method of claim 19, wherein the method further comprises providing a RPL14 gene probe.

21. The method of claim 1, wherein the 3p21 DNA probe is a CD39L3 gene probe.

22. The method of claim 1, wherein the 3p21 DNA probe is a PMGM gene probe.

23. The method of claim 1, wherein the 3p21 DNA probe is a GC20 gene probe.

24. The method of claim 19, wherein the 3p21 DNA probe is a CD39L3 gene probe.

25. The method of claim 19, wherein the 3p21 DNA probe is a PMGM gene probe.

26. The method of claim 19, wherein the 3p21 DNA probe comprises is a GC20 gene probe.

* * * * *